(12) United States Patent
Licari et al.

(10) Patent No.: US 7,648,976 B2
(45) Date of Patent: Jan. 19, 2010

(54) 17-ALLYLAMINO-17-DEMETHOXY-GELDANAMYCIN POLYMORPHS AND FORMULATIONS

(75) Inventors: Peter J. Licari, Fremont, CA (US); Timothy Leaf, Newark, CA (US); Ruchir P. Desai, Foster City, CA (US); Jorge L. Galazzo, Sunnyvale, CA (US); Greg O. Buchanan, Hayward, CA (US); Stephen William Watt, Chatteris (GB); Alexander Redvers Eberlin, Cambridge (GB); Robert Arslanian, Lafayette, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 108 days.

(21) Appl. No.: 11/595,005

(22) Filed: Nov. 8, 2006

(65) Prior Publication Data

US 2007/0203110 A1 Aug. 30, 2007

Related U.S. Application Data

(60) Provisional application No. 60/739,225, filed on Nov. 23, 2005, provisional application No. 60/809,527, filed on May 30, 2006.

(51) Int. Cl.
*C07D 225/04* (2006.01)
*C07D 225/06* (2006.01)
*A61K 9/00* (2006.01)

(52) U.S. Cl. .......................... 514/183; 540/463
(58) Field of Classification Search ................ 540/463; 514/183
See application file for complete search history.

(56) References Cited

U.S. PATENT DOCUMENTS

| | | | |
|---|---|---|---|
| 4,261,989 | A | 4/1981 | Sasaki |
| 5,510,118 | A | 4/1996 | Bosch |
| 5,534,270 | A | 7/1996 | De Castro |
| 5,662,883 | A | 9/1997 | Bagchi |
| 5,932,566 | A | 8/1999 | Schnur |
| 6,682,758 | B1 | 1/2004 | Tabibi |
| 6,872,715 | B2 | 3/2005 | Santi |
| 6,887,993 | B1 | 5/2005 | Tian |
| 6,890,917 | B2 | 5/2005 | Snader |
| 2004/0138160 | A1 | 7/2004 | Naito et al. |
| 2005/0020534 | A1 | 1/2005 | Johnson, Jr. |
| 2005/0020556 | A1 | 1/2005 | Johnson, Jr. |
| 2005/0020557 | A1 | 1/2005 | Johnson, Jr. |
| 2005/0020558 | A1 | 1/2005 | Johnson, Jr. |
| 2005/0026893 | A1 | 2/2005 | Johnson, Jr. |
| 2005/0043233 | A1 | 2/2005 | Stefanic et al. |
| 2005/0054589 | A1 | 3/2005 | Johnson, Jr. |
| 2005/0054625 | A1 | 3/2005 | Johnson, Jr. |
| 2005/0176695 | A1 | 8/2005 | Zhang |
| 2005/0256097 | A1 | 11/2005 | Zhong |
| 2006/0014730 | A1 | 1/2006 | Ulm |
| 2006/0067953 | A1 | 3/2006 | Mansfield |
| 2006/0148776 | A1 | 7/2006 | Ulm |

FOREIGN PATENT DOCUMENTS

| | | |
|---|---|---|
| WO | 2006034147 | 3/2006 |
| WO | WO 2006/034147 A2 | 3/2006 |
| WO | WO 2006/094029 A2 | 9/2006 |

OTHER PUBLICATIONS

Schnur et al. (1995), *J. Med. Chem.*, 38, 3806-3812, "Inhibition of Oncogene Products p185 (erbB-2) in Vitro and in Vivo by Geldanamycin and Dihydrogeldanamycin Derivatives."
Schnur et al. (1995), *J. Med. Chem.*, 38, 3813-3820, "erbB-2 Oncogene Inhibition by Geldanamycin Derivatives: Synthesis, Mechanism of Action, and Structure-Activity Relationships."
Jez et al., *Chemistry & Biology*, 10, 361-368 (2003), "Crystal Structure and Molecular Modeling of 17-DMAG in Complex with Human HSP90".
Stahl, "Drug Solubilization with Organic Solvents, Surfactants and Lipids," in Wermuth, ed., *The Practice of Medicinal Chemistry*, 2nd Ed., pp. 645-646 (Academic Press 2003).
Rabinow et al., *Nature Reviews Drug Discovery* 2004 3, 785-795, "Nanosuspensions in Drug Delivery".
Peters et al., *J. Antimicrobial. Chemotherapy* 2000 45, 77-83, "Preparation of Clofazimine Nanosuspension for Intravenous Use and Evaluation of Its Therapeutic Efficacy in Murine *Mycobacterium avium* Infection".
Itoh et al., *Chem. Pharm. Bull.* 2003 51 (2), 171-174, "Nanoparticle Formation of Poorly Water-Soluble Drugs from Ternary Ground Mixtures with PVP and SDS".
Burgess et al., *AAPS Journal* 2004, 6 (3), Article 20, "Particle Size Analysis: AAPS Workshop Report, Cosponsored by the Food and Drug Administration and the United States Pharmacopeia".
Tao et al., *Am. Assoc. Cancer Res.*, 96th Annual Meeting (Apr. 16-20, 2005), abstract No. 1435, "Preparation of Nanoparticle Albumin Bound 17-AAG (nab-17AAG) Suitable for Intravenous Injection" (abstract).
Konan et al., *Int. J. Pharm.* 2002 233 (1-2), 239-52, "Preparation and Characterization of Sterile and Freeze-Dried Sub-200 nm Nanoparticles" (abstract).
Quintanar-Guerreo et al., *J. Microencapsulation* 1998 15 (1), 107-119, "Influence of the Stabilizer Coating Layer on the Purification and Freeze-drying of Poly(D,L-lactic acid) Nanoparticles Prepared by an Emulsion-diffusion Process" (abstract).
Johnson et al., *J. Pharmaceutical Sci.* 2002, 91(4), 914-922, "Mannitol-Sucrose Mixtures—Versatile Formulations for Protein Lyophilization".
Tang et al., *Pharmaceutical Res.* 2004, 21(4), 191-200, "Design of Freeze-Drying Processes for Pharmaceuticals: Practical Advice".
Banerji et al., *Proc. Am. Soc. Clin. Oncol.* 22, 199 (2003, abstract 797), "A Pharmacokinetically (PK)- pharmacodynamically (PD) Guided Phase I Trial of the Heat Shock Protein 90 (HSP90) Inhibitor 17-Allyl-17- demethoxygeldanamycin (17AAG)" (abstract).
Goetz et al., *Eur. J. Cancer* 38 (Supp. 7), S54-S55 (2002), "A phase I trial of 17-Allyl-Amino-Geldanamycin (17-AAG) in patients with advanced cancer".
International Search Report and Written Opinion for International Application PCT/US06/40139.

*Primary Examiner*—Bruck Kifle
(74) *Attorney, Agent, or Firm*—Elliott Korsen Fox Rothschild LLP

(57) ABSTRACT

Polymorphs and pharmaceutical formulations of 17-allylamino-17-demethoxygeldanamycin (17-AAG).

47 Claims, 9 Drawing Sheets

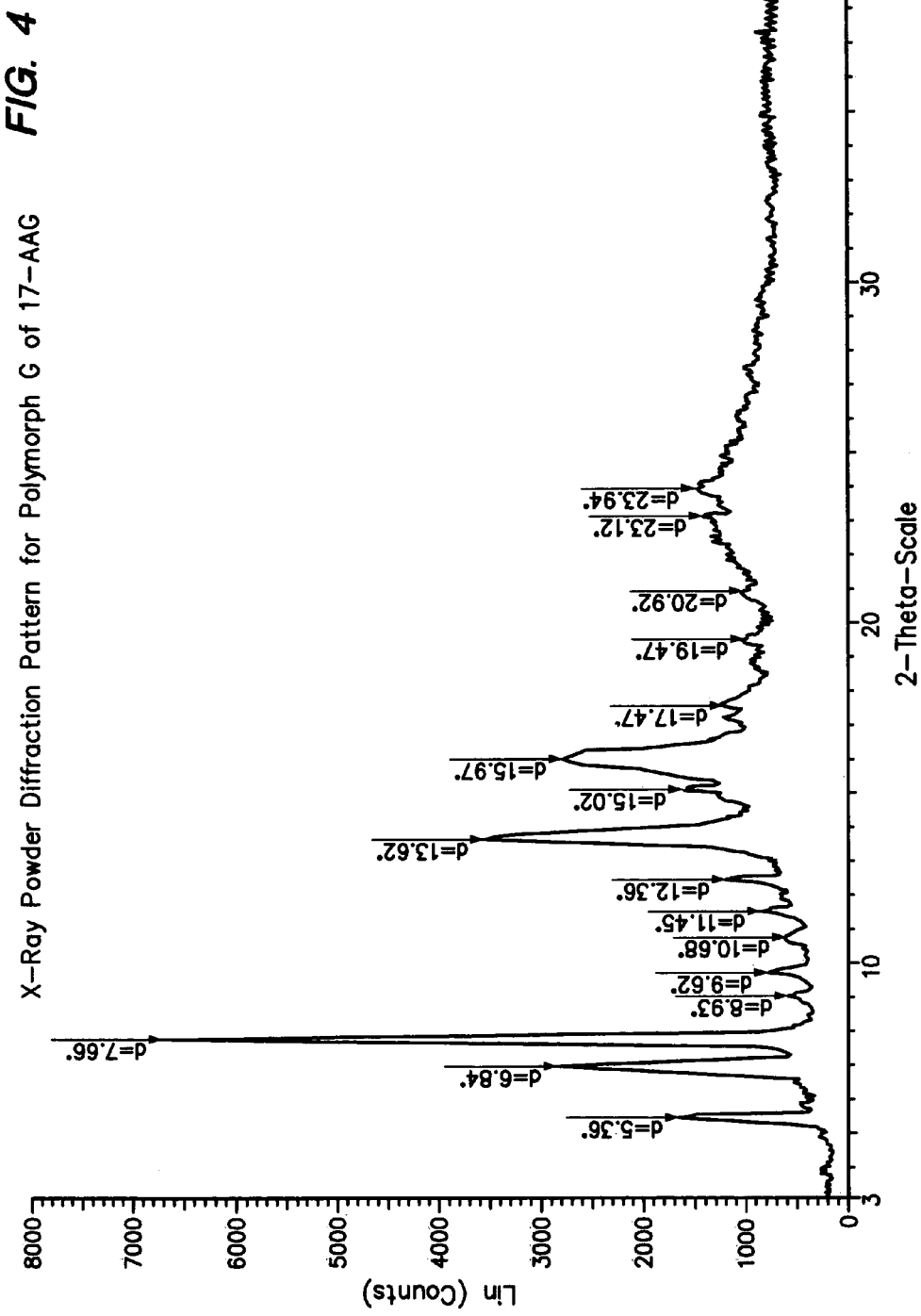

SEM Picture of 17-AAG Nanoparticles

17-ALLYLAMINO-17-DEMETHOXY-GELDANAMYCIN POLYMORPHS AND FORMULATIONS

CROSS-REFERENCE TO RELATED APPLICATIONS

This application claims the benefit under 35 U.S.C. §119(e) of U.S. Provisional Applications Nos. 60/739,225, filed Nov. 23, 2005, and 60/809,527, filed May 30, 2006, the disclosures of which are incorporated herein by reference.

BACKGROUND OF THE INVENTION

1. Field of the Invention

This invention relates to new 17-allylamino-17-demethoxygeldanamycin ("17-AAG") polymorphs, methods for making such new polymorphs, pharmaceutical formulations containing 17-AAG (especially formulations containing such new polymorphs), and methods for making and using such pharmaceutical formulations.

2. Description of Related Art

Geldanamycin belongs to the ansamycin natural product family, whose members are characterized by a macrolactam ring spanning two positions meta to each other on a benzenoid nucleus. Besides geldanamycin, the ansamycins include the macbecins, the herbimycins, the TAN-420s, and reblastatin.

Geldanamycin and its derivatives are the most extensively studied of the ansamycins. Although geldanamycin originally was identified as a result of screening for antibiotic activity, current interest resides primarily in its potential as an anticancer agent. It is an inhibitor of heat shock protein-90 ("Hsp90"), which is involved in the folding and activation of numerous proteins ("client proteins"), including key proteins involved in signal transduction, cell cycle control and transcriptional regulation. The binding of geldanamycin to Hsp90 disrupts Hsp90-client protein interactions, preventing the client proteins from being folded correctly and rendering them susceptible to proteasome-mediated destruction. Among the Hsp90 client proteins are many mutated or overexpressed proteins implicated in cancer: p53, Bcr-Abl kinase, Raf-1 kinase, Akt kinase, Npm-Alk kinase, Cdk4, Cdk6, Wee1, HER2/Neu (ErbB2), and hypoxia inducible factor-1α (HIF-1α). However, the hepatotoxicity and poor bioavailability of geldanamycin have led to its discontinuation as a clinical candidate.

Nevertheless, interest persists in the development of geldanamycin derivatives or analogs having geldanamycin-like bioactivity, but with a more pharmaceutically acceptable spectrum of properties. Position 17 of geldanamycin has been an attractive focal point, chemically speaking, for the synthesis of geldanamycin derivatives because its methoxy group is readily displaced by a nucleophile, providing a convenient synthetic pathway to the 17-substituted-17-demethoxygeldanamycins. Structure-activity relationship (SAR) studies have shown that chemically and sterically diverse 17-substituents can be introduced without destroying antitumor activity. See, e.g., Sasaki et al., U.S. Pat. No. 4,261,989 (1981) (hereinafter "Sasaki"); Schnur et al., U.S. Pat. No. 5,932,566 (1999); Schnur et al., *J. Med. Chem.* 1995, 38 (19), 3806-3812; Schnur et al., *J. Med. Chem.* 1995 38 (19), 3813-3820; and Santi et al., U.S. Pat. No. 6,872,715 B2 (2005); the disclosures of which are incorporated by reference. The SAR inferences are supported by the X-ray crystal co-structure of the complex between Hsp90 and a geldanamycin derivative, showing that the 17-substituent juts out from the binding pocket and into the solvent (Jez et al., *Chemistry & Biology* 2003, 10, 361-368). The best-known 17-substituted geldanamycin derivative is 17-AAG, first disclosed in Sasaki and currently undergoing clinical trials. Another noteworthy derivative is 17-(2-dimethylaminoethyl)-amino-17-demethoxygeldanamycin ("17-DMAG", Snader et al., U.S. Pat. No. 6,890,917 B2 (2005)), also in clinical trials.

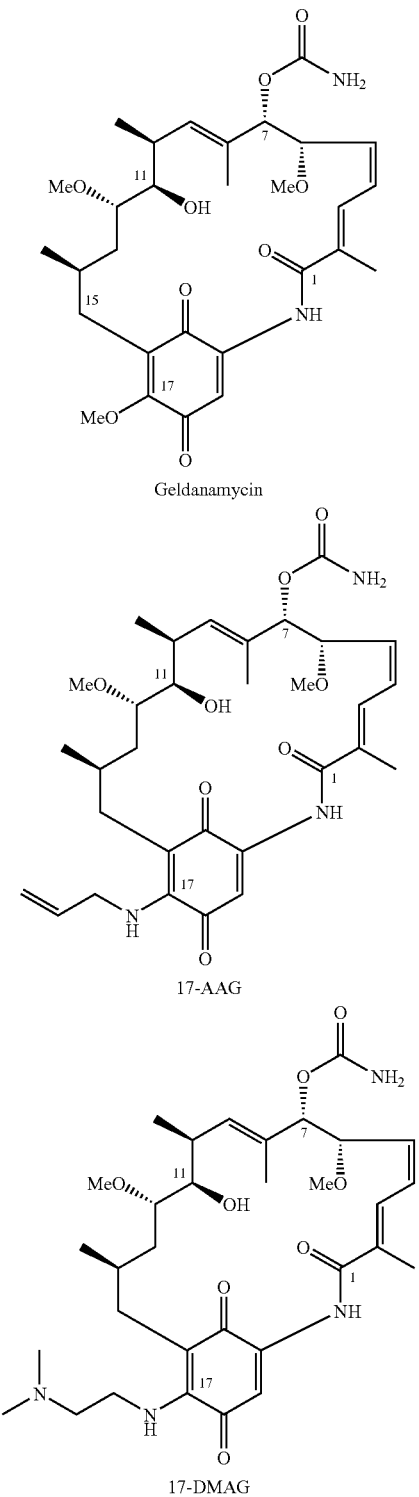

In preparing a pharmaceutical formulation, consideration must be given to the possible existence of polymorphs of the drug being formulated. If they exist, they may differ in their pharmaceutically relevant properties, including solubility, storage stability, hygroscopicity, density, and bioavailability. One polymorph may more or less spontaneously convert to another polymorph during storage. As a result of such conversion, a formulation designed to deliver a particular polymorph may end up containing a different polymorph that is incompatible with the formulation. A hygroscopic polymorph may pick up water during storage, introducing errors into weighing operations and affecting handleability. A preparation procedure designed for use with a particular polymorph may be unsuitable for use with a different polymorph. Even if no interconversion occurs, one polymorph may be easier to formulate than another, making selection of the right polymorph critical. Thus, polymorph choice is an important factor in designing a pharmaceutical formulation. (As used herein, the term "polymorph" includes amorphous forms and non-solvated and solvated crystalline forms, as specified in guideline Q6A(2) of the ICH (International Conference on Harmonization of Technical Requirements for Registration of Pharmaceuticals for Human Use).)

It is now known that 17-AAG is polymorphic. Sasaki originally disclosed a single form of 17-AAG melting at 212-214° C. Zhang et al., US 2005/0176695 A1 (2005) (hereinafter "Zhang") and Mansfield et al., US 2006/0067953 A1 (2006) (hereinafter "Mansfield") later reported that 17-AAG has a "high melt" form (mp 206-212° C.) and a "low-melt" form (mp 147-153° C.). The high melt form was the one initially obtained by Zhang and Mansfield in their syntheses 17-AAG and appears to be the same as the form reported by Sasaki, based on the closeness of the melting points. Zhang and Mansfield then reported preparing the low melt form from the high melt form by recrystallization from isopropanol. Mansfield includes X-ray powder diffraction (XRPD) and differential scanning calorimetry (DSC) data for both forms and discloses oral pharmaceutical formulations made with them. Mansfield further discloses that the low melt form is actually a mixture of two polymorphs and that it is his preferred form for use in pharmaceutical formulations.

A difficulty in the preparation of pharmaceutical formulations of ansamycins such as geldanamycin and 17-AAG, especially for parenteral administration, lies in their very low water solubility. (17-DMAG, with its alkylamino group, is more soluble.) To date, various techniques have been disclosed for formulating 17-AAG or geldanamycin:

(a) Tabibi et al., U.S. Pat. No. 6,682,758 B1 (2004) discloses 17-AAG formulated in a water-miscible organic solvent, (c) a surfactant, and (d) water. The water miscible solvent can be dimethylsulfoxide (DMSO), dimethylformamide, ethanol, glycerin, propylene glycol, or polyethylene glycol. The surfactant can be egg phospholipid.

(b) Ulm et al., US 2006/0014730 A1 (2006) discloses an emulsion-based pharmaceutical formulation for ansamycins based on medium chain triglycerides, an emulsifying agent (e.g., phosphatidylcholine), and a stabilizer (e.g., sucrose).

(c) Ulm et al., US 2006/0148776 (2006) discloses a pharmaceutical composition comprising 17-AAG, an emulsifying agent, and an oil comprising both medium and long chain triglycerides.

(d) Zhong et al., US 2005/0256097 A1 (2005), discloses a formulation of 17-AAG in a vehicle comprising (i) a first component that is ethanol; (ii) a second component that is a polyethoxylated castor oil (e.g., Cremophor™); and (iii) optionally a third component that is selected from the group consisting of propylene glycol, PEG 300, PEG 400, glycerol, and combinations thereof.

(e) Isaacs et al., WO 2006/094029 A2 (2006), discloses a pharmaceutical formulation comprising 17-AAG dissolved in a vehicle comprising an aprotic, polar solvent and an aqueous mixture of long chain triglycerides.

(f) Mansfield discloses a pharmaceutical formulation for oral administration, comprising an ansamycin and one or more pharmaceutically acceptable solubilizers, with the proviso that when the solubilizer is a phospholipid, it is present in a concentration of at least 5% w/w of the formulation. Other solubilizers disclosed include polyethylene glycols of various molecular weights, ethanol, sodium lauryl sulfate, Tween 80, Solutol® HS15, propylene carbonate, and so forth. Both dispersion and solution embodiments are disclosed.

(g) Desai et al., WO 2006/034147 A2 (2006), discloses the use of dimethylsorbide as a solvent for formulating poorly water-soluble drugs such as ansamycins.

For poorly water soluble drugs such as 17-AAG, an alternative to solvent-based formulations are formulations in which very small particles—sometimes referred to as nanoparticles—of the drug are dispersed in a medium. See, generally, Wermuth, ed., *The Practice of Medicinal Chemistry*, 2nd Ed., pp. 645-646 (Academic Press 2003); Ribnow et al., *Nature Reviews Drug Discovery* 2004 3, 785-795; Peters et al., *J. Antimicrobial. Chemotherapy* 2000 45, 77-83; Itoh et al., *Chem. Pharm. Bull.* 2003 51 (2), 171-174; Burgess et al, *AAPS Journal* 2004, 6 (3), Article 20; Bosch et al., U.S. Pat. No. 5,510,118 (1996); De Castro, U.S. Pat. No. 5,534,270 (1996); and Bagchi et al., U.S. Pat. No. 5,662,883 (1997), the disclosures of which are incorporated herein by reference.

With specific reference to 17-AAG, an albumin-based nanoparticulate formulation has been disclosed: Tao et al., *Am. Assoc. Cancer Res.*, 96th Annual Meeting (Apr. 16-20, 2005), abstract no. 1435. However, albumin may be pharmaceutically undesirable for an intravenous formulation. Mansfield, discussed supra, discloses a dispersion formulation of 17-AAG. Other patent documents generically reference the concept of making nanoparticle formulations of ansamycins (including, in certain cases, 17-AAG), but do not provide specific examples: Santi et al., U.S. Pat. No. 6,872,715 B2 (2005); Tian et al., U.S. Pat. No. 6,887,993 B1 (2005); Johnson, Jr., et al., US 2005/0020534 A1 (2005); Johnson, Jr., et al., US 2005/0020556 A1 (2005); Johnson, Jr., et al., US 2005/0020557 A1 (2005); Johnson, Jr., et al., US 2005/0020558 A1 (2005); Johnson, Jr., et al., US 2005/0026893 A1 (2005); Johnson, Jr., et al., US 2005/0054589 A1 (2005); and Johnson, Jr., et al., US 2005/0054625 A1 (2005); the disclosures of which are incorporated herein by reference.

The present invention provides new polymorphs of 17-AAG and pharmaceutical formulations made therefrom, in particular an especially desirable polymorph that is superior for the preparation of dispersion-based pharmaceutical formulations.

BRIEF SUMMARY OF THE INVENTION

This invention provides novel polymorphs of 17-AAG, including some that are especially suitable for use in suspension formulations. Two such suitable polymorphs are designated Polymorph C and Polymorph G, especially when used in their purified forms. Their preparation and characteristics are described in greater detail hereinbelow.

In another embodiment, there is provided a pharmaceutical suspension formulation comprising (a) 17-AAG comprising a polymorph selected from purified Polymorph C, purified Polymorph G, and combinations thereof and (b) at least one pharmaceutically acceptable excipient.

In the aforementioned suspension formulation, preferably
(A) the 17-AAG is present in an amount of between about 2.5 to about 75 weight percent as particles suspended in an aqueous medium, the 17-AAG having a particle size distribution between about 50 nm and about 3.0 microns with a median (volume distribution) particle size of between about 200 and about 400 nm, and
(B) the at least one pharmaceutically acceptable excipient comprises a surface active agent selected from the group consisting of (i) an ester of polyoxyethylenesorbitan and a $C_{12}$-$C_{20}$ fatty acid, the weight ratio of the ester to 17-AAG being between about 0.20 and about 1.0, (ii) a polyoxyethylene-polyoxypropylene block copolymer, the weight ratio of the block copolymer to 17-AAG being between about 0.5 and about 1.0, (iii) a phosphatidylcholine, the weight ratio of the phosphatidylcholine to the 17-AAG being between about 0.04 and about 0.1; and (iv) combinations thereof.

In another embodiment of the invention, there is provided a method for making a pharmaceutical suspension formulation, comprising homogenizing a mixture of
(a) 17-AAG comprising a polymorph selected from purified Polymorph C, purified G, and combinations thereof, in an amount of between about 2.5 and about 10 weight percent and
(b) a surface active agent selected from the group consisting of
  (i) an ester of polyoxyethylenesorbitan and a $C_{12}$-$C_{20}$ fatty acid, the weight ratio of the ester to 17-AAG being between about 0.20 and about 1.0,
  (ii) a polyoxyethylene-polyoxypropylene block copolymer, the weight ratio of the block copolymer to 17-AAG being between about 0.5 and about 1.0,
  (iii) a phosphatidylcholine, the weight ratio of the phosphatidylcholine to the 17-AAG being between about 0.04 and about 0.1; and
  (iv) combinations thereof,
until the particle size of the 17-AAG is reduced to a particle size distribution between about 50 nm and about 3.0 microns with a median (volume distribution) particle size of between about 200 and about 400 nm.

In another embodiment of the invention, there is provided a method for making a sterile pharmaceutical formulation, comprising the steps of
(a) providing a sterile composition comprising 17-AAG;
(b) aseptically combining the sterile composition comprising 17-AAG with a sterile solution of a surface active agent selected from the group consisting of (i) an ester of polyoxyethylenesorbitan and a $C_{12}$-$C_{20}$ fatty acid, (ii) a polyoxyethylene-polyoxypropylene block copolymer, (iii) a phosphatidylcholine, and (iv) combinations thereof to form a sterile mixture; and
(c) aseptically homogenizing the sterile mixture until the particle size of the 17-AAG is reduced to a particle size distribution between about 50 nm and about 3.0 microns with a median (volume distribution) particle size of between about 200 and about 400 nm.

In the above formulations and methods, the amount of 17-AAG is preferably is between about 2.5 and 20, more preferably between about 2.5 and 10, and most preferably between about 4 and about 6 weight percent, based on total formulation weight.

In another aspect of the invention, there is provided a method of administering 17-AAG to a subject in need of treatment with 17-AAG, comprising administering intravenously to such subject a pharmaceutical formulation of this invention.

In another embodiment of the invention, there is provided a method for preparing purified 17-AAG, comprising the steps of (a) preparing a solution of 17-AAG in refluxing acetone; (b) cooling the solution to a temperature in the range between about 18 and about 30° C.; (c) precipitating the 17-AAG by the addition of an antisolvent portionwise; and (d) collecting the precipitated 17-AAG. 17-AAG so purified will have been significantly purged of non-17-AAG impurities and can be used for preparing Polymorphs C or G.

In another embodiment, there is provided a method for making purified Polymorph C of 17-AAG, comprising the steps of:
(a) providing a solution of 17-AAG in acetone, at reflux;
(b) adding to the solution a volume of water substantially equal to the volume of the solution, at a rate allowing the solution to remain at reflux;
(c) distilling off the acetone until substantially all the acetone has been distilled off, during which distillation purified Polymorph C precipitates; and
(d) collecting the purified Polymorph C.

In another embodiment, there is provided purified Polymorph C of 17-AAG, made by the foregoing method.

BRIEF DESCRIPTION OF THE DRAWING(S)

FIGS. 1, and 2 are an XRPD pattern and an infrared spectrum, respectively, of purified Polymorph C of 17-AAG.

FIGS. 3*a* and 3*b* are DSC scans of two different samples of purified Polymorph C of 17-AAG.

FIGS. 4, 5, and 6 are an XRPD pattern, an IR spectrum, and a DSC scan, respectively, of purified Polymorph G of 17-AAG.

DETAILED DESCRIPTION OF THE INVENTION

17-AAG Polymorphs

Figure 1:
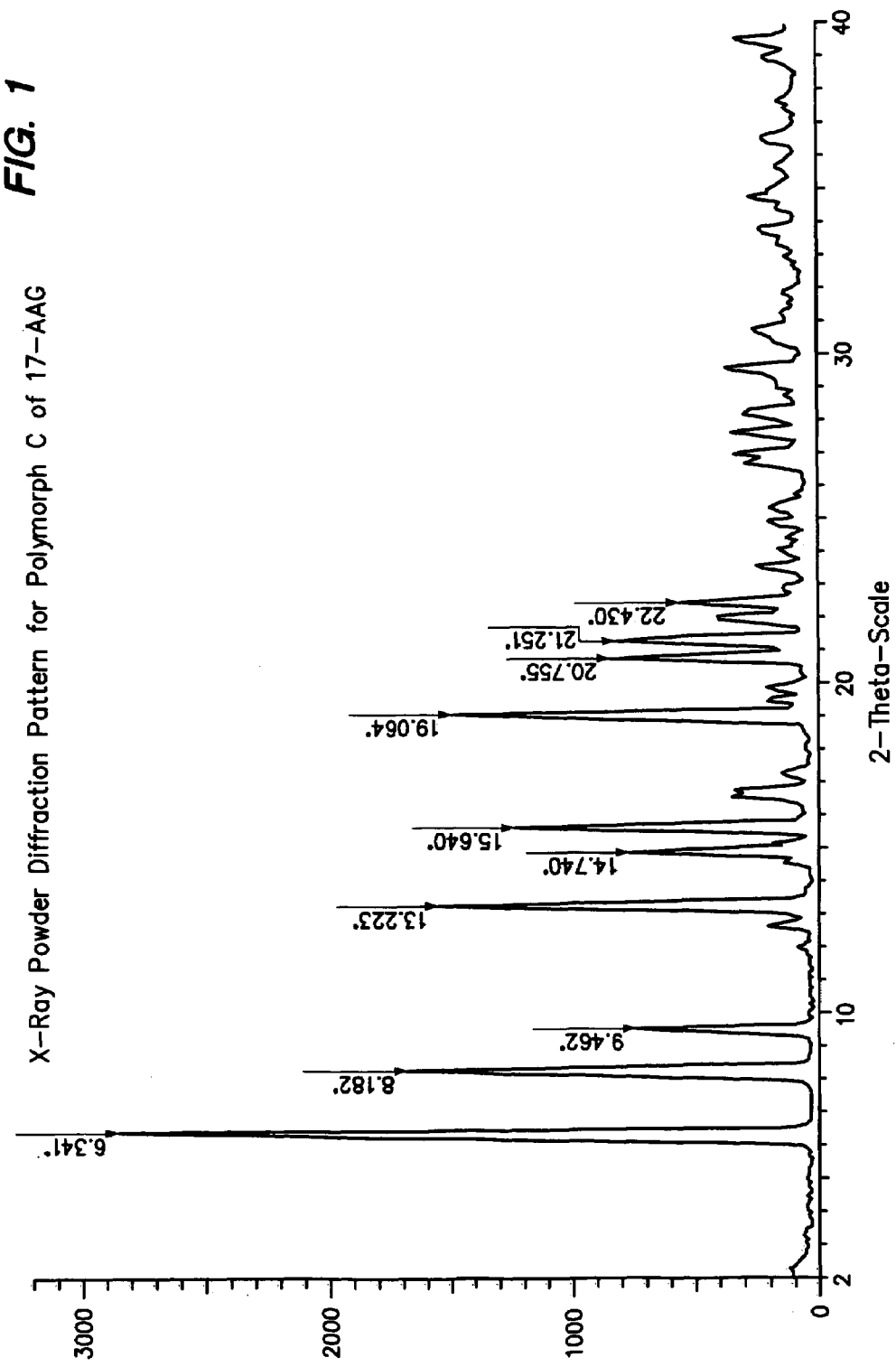

Geldanamycin is a well-known natural product, obtainable by culturing *Streptomyces hygroscopicus* var. *geldanus* NRRL 3602. 17-AAG is made semi-synthetically, by the reaction of allylamine with geldanamycin, as described in Sasaki. Both geldanamycin and 17-AAG also are available commercially.

17-AAG is polymorphic and exists in multiple forms, many of which are solvates. We have generated many polymorphs using a variety of solvents and crystallization conditions. The polymorphs were characterized by techniques such as XRPD, DSC, infrared spectroscopy, gravimetric vapor sorption (GVS), $^1$H-NMR, polarized light microscopy (PLM), and thermogravimetric analysis (TGA). We grouped the polymorphs according to similarities in XRPD data, with summary descriptions provided below. Polymorphs that are solvated are referred to by group and solvate names, as in "Polymorph A (DMF solvate)" or "the DMF solvate of Polymorph A".

Group A The N,N-dimethylformamide (DMF), ethyl acetate (EtOAc), and methyl isobutyl ketone (MIBK) solvates of Polymorph A all have XRPD peaks at about 5.6, 7.0, 9.2, 11.2, 16.4, and 17.9 degrees 2θ (the first four being its lowest angle peaks). DSC shows transitions (possibly desolvations) with onset temperatures ranging from 144° C. for the EtOAc solvate to 168° C. for the DMF solvate. Upon heating, variable temperature XRPD (VT-XRPD) and DSC show that Polymorphs A are converted to the more stable Polymorph C.

Group B Polymorph B has its first eight lowest angle XRPD peaks at about 5.9, 6.3, 7.2, 7.5, 9.3, 9.8, 11.6, and 12.5 degrees 2θ. VT-XRPD shows that, upon heating, Polymorph B is converted to Polymorph C.

Group C Polymorph C is a non-solvated polymorph. Of the 17-AAG polymorphs identified by us, it is the most stable to moisture and heat. It has characteristic XRPD peaks at about 6.4, 8.3, 9.6, 13.3, 14.9, 15.7, 19.1, and 20.8 degrees 2θ. The DSC thermograms of Polymorph C show an endotherm with an onset temperature of about 188 to about 205° C., without any thermal events noticeable at lower temperatures. Polymorph C does not convert to any other polymorph upon heating.

Group D Polymorph D (dichloromethane solvate) has XRPD peaks at about 3.9, 4.6, 5.7, and 7.9 degrees 2θ, the first three being its lowest angle peaks. Upon heating, it converts to Polymorph C.

Group E The anisole, t-butyl methyl ether and dimethylsulfoxide solvates of Polymorph E have characteristic XRPD peaks at about 4.2, 5.8, 7.8, 8.8, 9.2, 13.1, and 13.7 degrees 2θ, with the first five being its lowest angle peaks. DSC thermograms showed endothermic transitions with onset temperatures at about 143, 147, and 145° C., respectively. Typically, this polymorph group is prepared using high boiling solvents. After melting, these polymorphs exist in a molten state until decomposition at about 220° C. However, conversion to Polymorph C is observed at 40° C. and 70% relative humidity (RH).

Group G Polymorph G group has characteristic XRPD peaks at about 5.4, 6.8, 7.7, 8.9, 9.6, 10.7, and 13.6 degrees 2θ, with the first six being its lowest angle peaks. Heating converts Polymorph G to Polymorph C.

Among these polymorphs, Polymorph C is the most stable to heat and humidity. Many of the other ones are unstable or are converted to Polymorph C by heat and/or humidity. For these reasons, Polymorph C is an especially preferred polymorph for pharmaceutical formulations. Further, we have discovered that Polymorph C produces the most stable nanoparticulate suspension formulations, as shown hereinbelow. As shown by the data below, Polymorph G also produces stable nanoparticulate suspension formulations and thus is also a preferred polymorph.

Highly pure 17-AAG, usually more than 95% pure and preferably more than 97% pure (free of chemical impurities, i.e., components that are not 17-AAG) and suitable for conversion into purified Polymorph C or purified Polymorph G, can be prepared by first making a solution of 17-AAG in refluxing acetone, cooling the solution to approximately ambient temperature (i.e., about 18 to about 30° C.), precipitating the 17-AAG by the addition of an antisolvent such as water over a period of about 1 h (though a shorter or longer period can be used, e.g., 15 min to 24 h), and collecting the precipitated 17-AAG.

In an alternative procedure for preparing purified 17-AAG, a solution of 17-AAG in acetone is prepared. A volume of water approximately equal to the volume of the solution is added, at a temperature between about 18 and about 30° C. The purified 17-AAG is allowed to precipitate out of solution, with stirring, and collected. The stirring can be maintained for a period from about 15 min to about 24 h.

A preferred method for making purified Polymorph C (i.e., converting another 17-AAG polymorph into Polymorph C) comprises the steps of:
(a) providing a solution of 17-AAG in acetone, at reflux;
(b) adding to the solution a volume of water substantially equal to the volume of the solution, at a rate allowing the solution to remain at reflux;
(c) distilling off the acetone until the pot temperature reaches or exceeds 95° C., during which Polymorph C crystals form in the solution; and
(d) collecting the Polymorph C crystals as purified Polymorph C.

The refluxing acetone solution of 17-AAG can be prepared by dissolving the 17-AAG in a volume of refluxing acetone or by dissolving the 17-AAG in a volume of acetone at room temperature and bringing the solution up to reflux. After an approximately equal volume of water is added, the acetone is removed by distillation at atmospheric pressure. Distillation is continued until the pot and vapor temperatures are both at about the boiling point for water (i.e., about 100° C. for operations conducted at sea level) or just below it (e.g., about 95° C.), at which point substantially all the acetone will have been removed. As the acetone distills, 17-AAG phase separates (precipitates or crystallizes) out of solution as suspended Polymorph C. The Polymorph C crystals can be collected by cooling the suspension to ambient (room) temperature, filtering, and washing with 1:1 acetone water. The collected crystals can be dried in vacuo, for example in a vacuum oven at 40° C. for 12 h.

Another method for making Polymorph C—albeit not as desirable because the crystallinity of the product is lower—comprises heating 17-AAG at a temperature between about 70 and about 100° C. for a period of between 1 and 18 h.

A representative XRPD pattern for purified Polymorph C is shown in FIG. 1, this particular pattern being that of a highly crystalline and pure sample. Table I numerically summarizes data from the XRPD of FIG. 1, including its three lowest 2θ angle peaks and several additional peaks useful for characterizing Polymorph C. Polymorph C can be defined by its XRPD peaks at 6.4±0.3, 8.3±0.3, 9.6±0.3, 13.3±0.3, 14.9±0.3, 15.7±0.3, 19.1±0.3, and 20.8±0.3 degrees 2θ, with the first three being its lowest angle peaks and the remaining ones being the next few most intense peaks, such peaks being the most relevant ones for defining Polymorph C. The peak at 21.3±0.3 degrees 2θ can be used as a further diagnostic peak.

TABLE I

XRPD Data for Purified Polymorph C of 17-AAG

| Peak No. | Angle 2θ (degrees) | Relative Intensity (%) |
|---|---|---|
| 1 | 6.3 | 100 |
| 2 | 8.2 | 59 |
| 3 | 9.5 | 26 |
| 4 | 12.7 | 10 |
| 5 | 13.2 | 54 |
| 6 | 14.7 | 27 |
| 7 | 15.6 | 43 |
| 8 | 19.1 | 53 |
| 9 | 20.8 | 30 |
| 10 | 21.3 | 29 |

Figure 2:
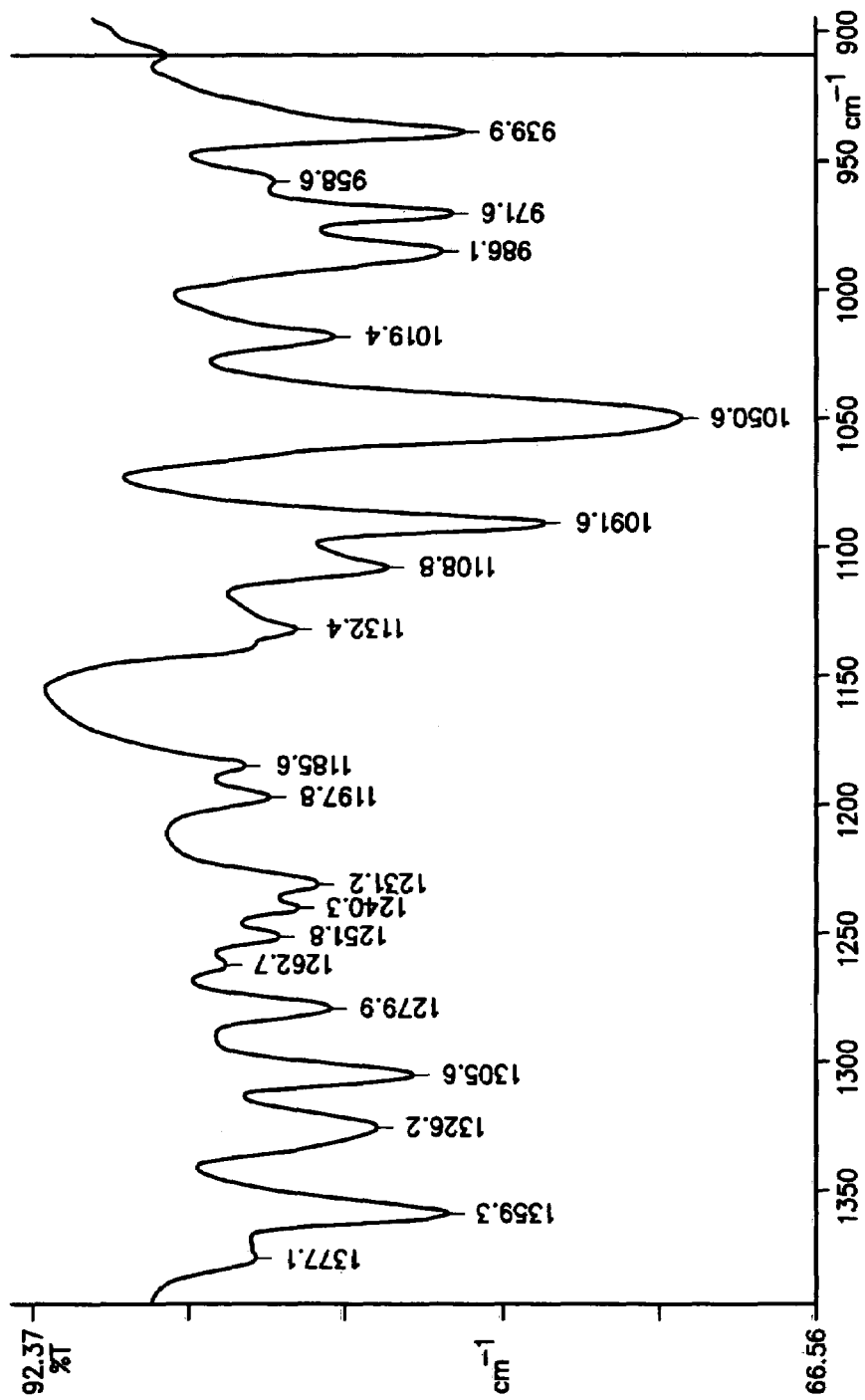

FIG. 2 shows the infrared spectrum of a highly crystalline and pure sample of Polymorph C.

Figure 3A:
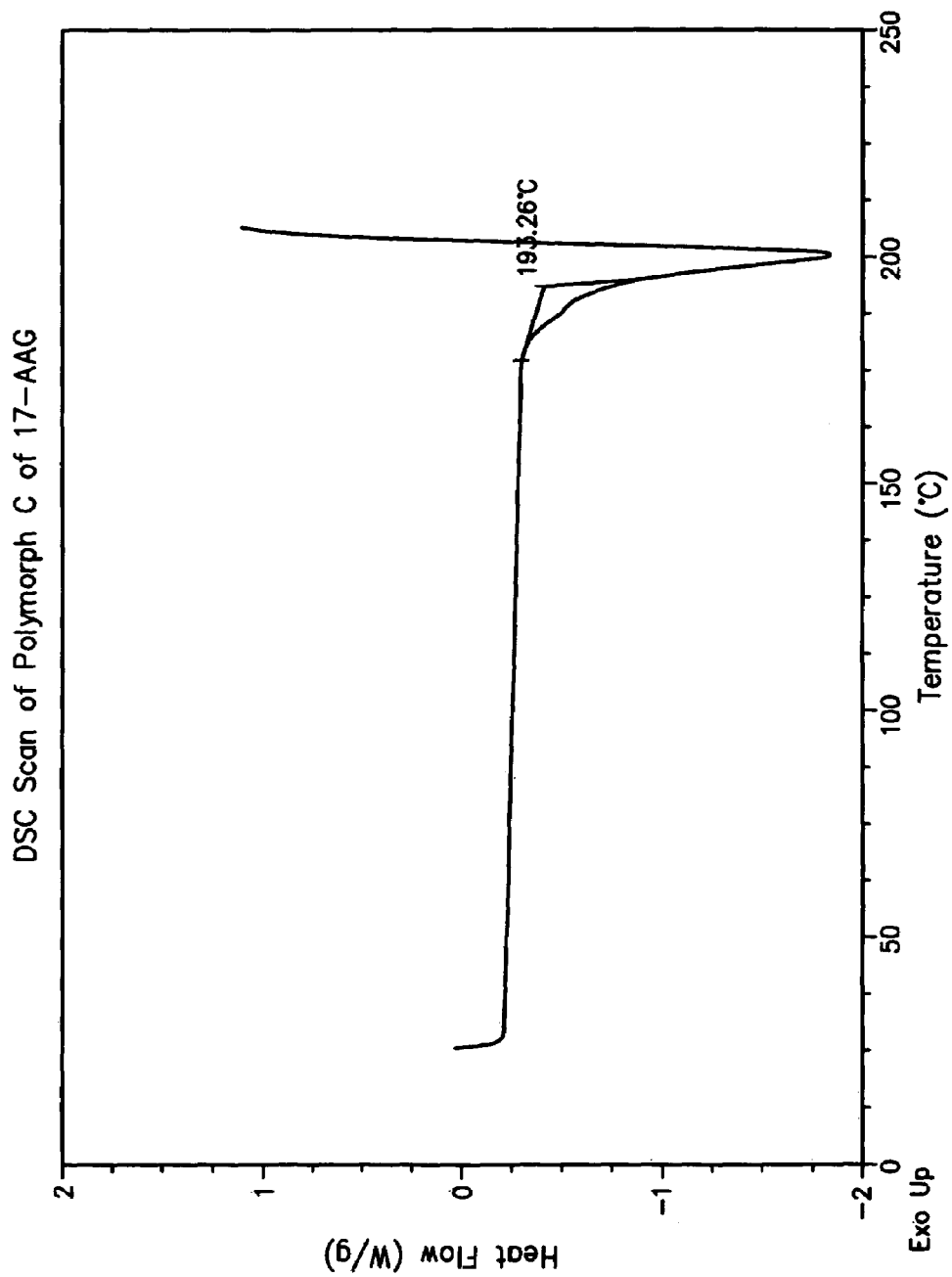
Figure 3B:
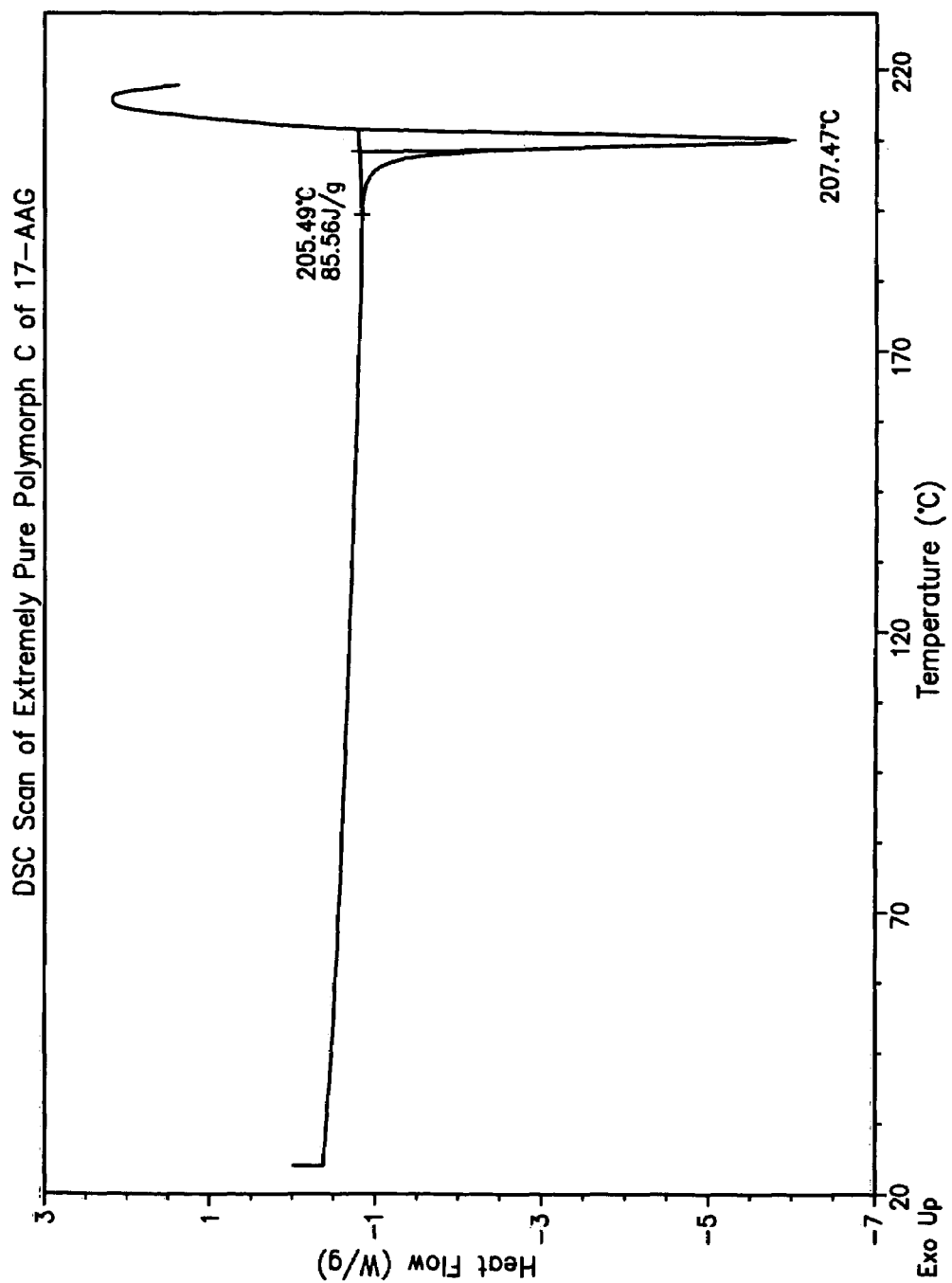

A representative DSC trace for purified Polymorph C is reproduced in FIG. 3a, showing an endothermic transition (melting point) with an onset temperature at about 193° C., without any desolvation transitions at a lower temperature, consistent with its identification as an unsolvated polymorph. Those skilled in the art will appreciate that DSC transitions will vary somewhat from experiment to experiment depending on factors such as sample purity and rate of heating. To illustrate, FIG. 3b shows the DSC scan for a exceptionally highly pure sample (both in terms of being free of non-17-AAG materials and of other polymorphs of 17-AAG) of Polymorph C, with an endothermic transition having an onset temperature of about 205° C. Thus, Polymorph C can be characterized DSC-wise by an endothermic transition having an onset temperature in the range between about 188 and about 205° C., without the occurrence of any other DSC thermal events (e.g., desolvation) at a lower temperature. In contrast, Mansfield reported DSC melt transitions at 156 and 172° C. for his low melt form and at 204° C. for his high melt form, indicating that his forms are distinguishable from polymorphs of this invention.

Figure 5:
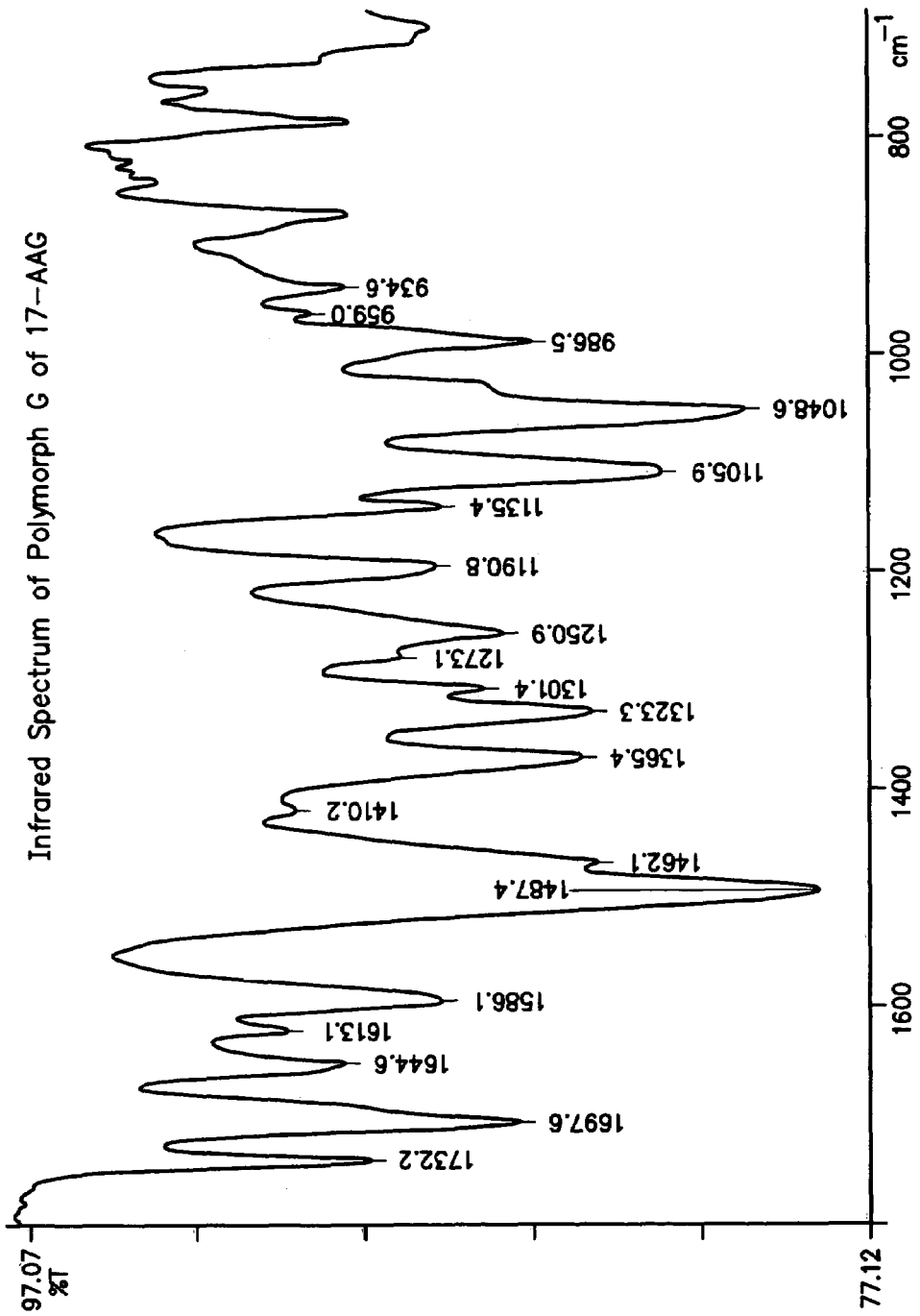
Figure 6:
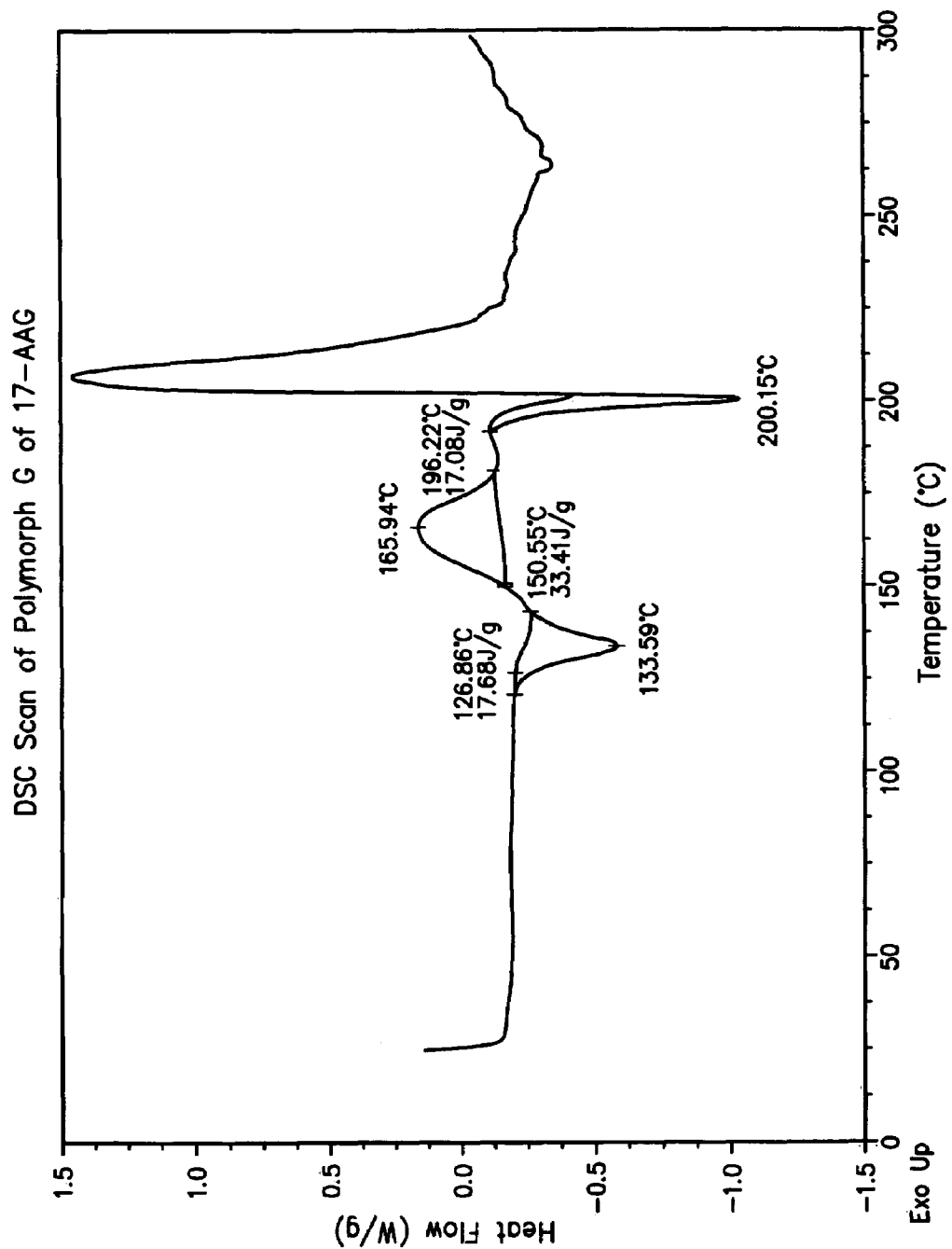

Purified Polymorph G can be prepared by several different routes. In one route, a solution of 17-AAG in acetone is poured into water with stirring, and stirring is continued for a few minutes. The crystals are harvested by filtration and vacuum dried. In another method, water is added gradually over a period of time such as 50 min. The crystals are similarly harvested and dried. FIG. 4 shows an XRPD pattern for purified Polymorph G, which can be defined by its six lowest angle peaks at 5.4±0.3, 6.8±0.3, 7.7±0.3, 8.9±0.3, 9.6±0.3, and 10.7±0.3 degrees 2θ and by a peak at 13.6±0.3 degrees 2θ. FIG. 5 is an infrared spectrum of purified Polymorph G, while FIG. 6 is a DSC scan of purified Polymorph G, showing an endothermic transition with an onset temperature of about 196° C., but with several transitions at lower temperatures.

To provide a comparison between the polymorphs of this invention and prior art polymorphs, Table II juxtaposes XRPD data for Polymorphs C and G against XRPD data reported by Mansfield for his high melt and low melt forms, listing the first ten significant peaks of each. As is evident from the table, Polymorphs C and G and Mansfield's forms have distinctly different XRPD patterns, showing that Polymorphs C and G are novel. Particularly noteworthy are the differences in the first several lowest angle peaks, which are generally regarded in the art as the most diagnostically useful peaks.

TABLE II

Comparison of XRPD Patterns for 17-AAG Forms

| | Angle (degrees 2θ) | | | |
|---|---|---|---|---|
| Peak No. | Polymorph C | Polymorph G | Mansfield (high melt) | Mansfield (low melt) |
| 1 | 6.3 | 5.4 | 6.08 | 4.35 |
| 2 | 8.2 | 6.8 | 7.40 | 5.85 |
| 3 | 9.5 | 7.7 | 11.84 | 7.90 |
| 4 | 13.2 | 8.9 | 12.48 | 9.00 |
| 5 | 14.7 | 9.6 | 13.88 | 11.64 |
| 6 | 15.6 | 10.7 | 16.31 | 14.70 |
| 7 | 19.1 | 11.5 | 17.32 | — |
| 8 | 20.8 | 12.4 | 18.16 | — |
| 9 | 21.3 | 13.6 | 22.24 | — |
| 10 | 22.4 | 15.0 | 23.13 | — |

Generally, Polymorphs C or G can be purified as a result of a preparation procedure that converts another polymorph of 17-AAG into them or as a result of a separation process to remove other polymorphs of 17-AAG. Additionally, other impurities may have been removed as a result of such purification. Preferably, purified Polymorph C contains a predominant amount of Polymorph C, to the exclusion of other 17-AAG polymorphs. Similarly, purified Polymorph G preferably contains a predominant amount of Polymorph G, to the exclusion of other polymorphs of 17-AAG. More preferably, purified Polymorph C (or Polymorph G, as the case may be) is substantially free of other polymorphs of 17-AAG, meaning that little or none of the other polymorphs are detectable by XRPD. Also preferably, purified Polymorph C or Polymorph G are substantially chemically pure, meaning that they contain 5% or less of chemical impurities (components that are not 17-AAG).

In one embodiment, purified Polymorph C is a composition comprising 17-AAG, the composition being characterized by an XRPD pattern having its three lowest angle peaks at 6.4±0.3, 8.3±0.3, and 9.6±0.3 degrees 2θ and further having peaks at 13.3±0.3, 14.9±0.3, 15.7±0.3, 19.1±0.3, and 20.8±0.3 degrees 2θ.

In another embodiment, purified Polymorph C is a composition comprising 17-AAG, wherein the 17-AAG is present in the composition predominantly in the form of Polymorph C characterized by an XRPD pattern having its three lowest angle peaks at 6.4±0.3, 8.3±0.3, and 9.6±0.3 degrees 2θ and further having peaks at 13.3±0.3, 14.9±0.3, 15.7±0.3, 19.1±0.3, and 20.8±0.3 degrees 2θ.

In one embodiment, purified Polymorph G is a composition comprising 17-AAG, the composition being characterized by an XRPD pattern having its six lowest angle peaks at 5.4±0.3, 6.8±0.3, 7.7±0.3, 8.9±0.3, 9.6±0.3, and 10.7±0.3 degrees 2θ and further having a peak at 13.6±0.3 degrees 2θ.

In another embodiment, purified Polymorph G is a composition comprising 17-AAG, wherein the 17-AAG is present in the composition predominantly in the form of Polymorph G characterized by an XRPD pattern having its six lowest angle peaks at 5.4±0.3, 6.8±0.3, 7.7±0.3, 8.9±0.3, 9.6±0.3, and 10.7±0.3 degrees 2θ and further having a peak at 13.6±0.3 degrees 2θ.

Formulations

Generally, we have found that the ability to prepare a successful nanoparticulate formulation employing purified Polymorph C or G is not dependent on the initial particle size—that is, it is not necessary to pre-reduce the particle size of the 17-AAG by micronization or other similar process before homogenization. The 17-AAG particles simply must be sufficiently small to pass through the narrowest point of the homogenization flow path, typically on the order of less than about 500 μm.

Nanoparticulate formulations of this invention have a 17-AAG particle size distribution between about 50 nm and about 3.0 microns, preferably between about 50 nm and about 2.0 microns, more preferably between about 50 nm and about 1.2 micron. The median (volume distribution) particle size is between about 200 and about 400 nm, preferably between about 250 and about 350 nm. Particle size distributions can be measured by a suitable particle size analyzer such as Nanotrac 250 (Microtrac, Inc., Montgomeryville, Pa., USA) or Zetasizer Nano (Malvern Instruments Ltd., Worcestershire, UK).

Where the surface active agent is an ester of polyoxyethylenesorbitan and a $C_{12}$-$C_{20}$ fatty acid, the latter can be saturated or unsaturated. Examples of suitable fatty acids include lauric, linoleic, linolenic, oleic, palmitic, palmitoleic, and stearic acids. The polyoxyethylenesorbitan can be singly or multiply esterified with the $C_{12}$-$C_{20}$ fatty acid. Suitable esters of polyoxyethylenesorbitan with a $C_{12}$-$C_{20}$ fatty acid include: polyoxyethylenesorbitan monooleate (polyethylene glycol sorbitan monooleate, polysorbate 80 or TWEEN® 80); polyoxyethylenesorbitan monolaurate (polyethylene glycol sorbitan monolaurate or TWEEN® 20); polyoxyethylenesorbitan monopalmitate (polyethylene glycol sorbitan monopalmitate or TWEEN® 40); polyoxyethylenesorbitan monostearate (polyethylene glycol sorbitan monostearate or TWEEN® 60); polyoxyethylenesorbitan trioleate (polyethylene glycol trioleate or TWEEN® 85); and polyoxyethylenesorbitan tristearate (polyethylene glycol sorbitan tristearate or TWEEN® 65); with the first two being preferred and the first one being especially preferred. The weight ratio of the ester to 17-AAG preferably is between about 0.20 and about 1.0, more preferably between about 0.20 and about 0.35.

Where the surface active agent is polyoxyethylene-polyoxypropylene block copolymer, a commercially available version is Pluronic® F-68. The weight ratio of the copolymer to 17-AAG preferably is between about 0.5 to about 1.0.

Where the surface active agent is phosphatidylcholine (also known as lecithin), it can be derived from sources such as soybean or egg, with the former being preferred. The weight ratio of phosphatidylcholine to 17-AAG preferably is between about 0.04 and about 0.1, more preferably between about 0.04 and about 0.06. A specific phosphatidylcholine that can be used is Phospholipon® 90G, which is phosphatidylcholine of soybean provenance.

Combinations of two or more different surface active agents can be used, for example two different esters of polyoxyethylenesorbitan and a $C_{12}$-$C_{20}$ fatty acid or one such ester and a polyoxyethylene-polyoxypropylene block copolymer. A preferred combination of surface active agents is (A) a polyoxyethylenesorbitan and a $C_{12}$-$C_{20}$ fatty acid or polyoxyethylene-polyoxypropylene block copolymer and (B) a phosphatidylcholine.

Preferably, the homogenizing step is effected by high-pressure homogenization under high shear conditions, such as by forcing the mixture through a small orifice (e.g., 50 to 125, preferably 80 to 100, microns in diameter) at pressures between 1,000 and 45,000 psi, preferably pressures of about 18,000 to about 23,000 psi), using multiple passes as needed. Any number of apparatuses can be used, including microfluidizers, mills, and the like.

Optionally, formulations of this invention further comprise a carbohydrate, such as a mono- and/or disaccharide or combinations thereof. If used, the final formulation preferably contains by weight between about 5 and about 15 weight % of total carbohydrate. By way of illustration, the final formulation can contain 10 weight % sucrose or a combination of 4 weight % mannitol and 1 weight % sucrose (for a total carbohydrate content of 5 weight %). The carbohydrate can be selected from the group consisting of sucrose, mannitol, lactose, trehalose, dextrose, and combinations thereof, with sucrose being preferred.

The formulations of this invention can be lyophilized (freeze-dried) and stored as a lyophilate for later reconstitution. In such instance, the use of a carbohydrate is preferred, to serve as a cryoprotectant and/or lyoprotectant. Exemplary disclosures relating to lyophilization of pharmaceutical formulations include Konan et al., *Int. J. Pharm.* 2002 233 (1-2), 293-52; Quintanar-Guerreo et al., *J. Microencapsulation* 1998 15 (1), 107-119; Johnson et al., *J. Pharmaceutical Sci.* 2002, 91 (4), 914-922; and Tang et al., *Pharmaceutical Res.* 2004, 21 (4), 191-200; the disclosures of which are incorporated herein by reference.

As an alternative to lyophilization, a formulation of this invention can be stored frozen and then thawed, reconstituted, and diluted before administration. In such instance, the use of a carbohydrate such as sucrose as a cryoprotectant is preferred.

Where the final nanoparticulate formulation needs to be sterile, we have found it impractical to heat sterilize (autoclave) the formulation itself, because the procedure causes changes in particle size distribution. Nor was it feasible to filter-sterilize the formulation, because of the size of the 17-AAG particles. We solved this problem by separately sterilizing the 17-AAG (e.g., by autoclaving a suspension of 17-AAG in water or by sterile crystallization) and the other components (e.g., polysorbate 80, phosphatidylcholine, carbohydrate, etc.) individually or in combination using techniques established in the art, such as sterile filtration or autoclaving, followed by aseptic combination of the formulation components and performance of the processing steps.

We have found it to be more convenient to prepare the formulation at an initial concentration that is more concentrated than that actually administered, reducing the volume of material to be handled during storage and shipping. Then the formulation is diluted shortly before administration—for example by about 10× to 20× into a suitable vehicle such as water for injection (WFI) or 5% dextrose in water (D5W)—and administered, typically within 12 to 24 h of dilution. However, if desired, the formulation can be prepared directly at the final administration concentration.

The formulation can be administered to a subject by an appropriate method, such as parenterally (especially intravenously). Alternatively, oral administration is also contemplated. Because it does not entail use of an excipient that potentially causes hypersensitivity reactions in patients (such as Cremophor®), it represents a safer product. The osmolality of a diluted formulation ready for infusion (approximately 260 mmol/kg) is similar to physiological conditions. Because the formulation contains a higher concentration of 17-AAG a smaller volume is administered, with a concomitant shorter administration time.

INDUSTRIAL APPLICABILITY

17-AAG can be used to treat a variety of proliferative disorders, such as, but not limited to, hyperproliferative diseases, including: cancers of the head and neck which include tumors of the head, neck, nasal cavity, paranasal sinuses, nasopharynx, oral cavity, oropharynx, larynx, hypopharynx, salivary glands, and paragangliomas; cancers of the liver and biliary tree, particularly hepatocellular carcinoma; intestinal cancers, particularly colorectal cancer; treat ovarian cancer; small cell and non-small cell lung cancer; breast cancer sarcomas, such as fibrosarcoma, malignant fibrous histiocytoma, embryonal rhabdomysocarcoma, leiomysosarcoma, neurofibrosarcoma, osteosarcoma, synovial sarcoma, liposarcoma, and alveolar soft part sarcoma; neoplasms of the central nervous systems, particularly brain cancer; lymphomas such as Hodgkin's lymphoma, lymphoplasmacytoid lymphoma, follicular lymphoma, mucosa-associated lymphoid tissue lymphoma, mantle cell lymphoma, B-lineage large cell lymphoma, Burkitt's lymphoma, and T-cell anaplastic large cell lymphoma. More particularly, cancers that can be targeted for treatment by 17-AAG include breast cancer, multiple myeloma, melanoma, colon cancer, lung cancer (especially non-small cell lung cancer (NSCLC)), prostate cancer, thyroid cancer, ovarian cancer, lymphoma, pancreatic cancer, and leukemia (especially chronic myelogenous leukemia (CML) and chronic lymphocytic leukemia or (CLL)).

Non-cancer disorders that are characterized by cellular hyperproliferation can also be treated by 17-AAG administered in accordance with this invention. Illustrative examples of such disorders include but are not limited to: atrophic gastritis, inflammatory hemolytic anemia, graft rejection, inflammatory neutropenia, bullous pemphigoid, coeliac disease, demyelinating neuropathies, dermatomyositis, inflammatory bowel disease (ulcerative colitis and Crohn's disease), multiple sclerosis, myocarditis, myositis, nasal polyps, chronic sinusitis, pemphigus vulgaris, primary glomerulonephritis, psoriasis, surgical adhesions, stenosis or restenosis, scleritis, scleroderma, eczema (including atopic dermatitis, irritant dermatitis, allergic dermatitis), periodontal disease (i.e., periodontitis), polycystic kidney disease, and type I diabetes. Other examples include vasculitis (e.g., Giant cell arteritis (temporal arteritis, Takayasu's arteritis), polyarteritis nodosa, allergic angiitis and granulomatosis (Churg-Strauss disease), polyangitis overlap syndrome, hypersensitivity vasculitis (Henoch-Schonlein purpura), serum sickness, drug-induced vasculitis, infectious vasculitis, neoplastic vasculitis, vasculitis associated with connective tissue disorders, vasculitis associated with congenital deficiencies of the complement system, Wegener's granulomatosis, Kawasaki's disease, vasculitis of the central nervous system, Buerger's disease and systemic sclerosis); gastrointestinal tract diseases (e.g., pancreatitis, Crohn's disease, ulcerative colitis, ulcerative proctitis, primary sclerosing cholangitis, benign strictures of any cause including ideopathic (e.g., strictures of bile ducts, esophagus, duodenum, small bowel or colon); respiratory tract diseases (e.g., asthma, hypersensitivity pneumonitis, asbestosis, silicosis and other forms of pneumoconiosis, chronic bronchitis and chronic obstructive airway disease); nasolacrimal duct diseases (e.g., strictures of all causes including ideopathic); and eustachean tube diseases (e.g., strictures of all causes including ideopathic).

17-AAG can be administered in combination with another active pharmaceutical ingredient (API), such as other anti-cancer or cytotoxic agents including alkylating agents, angiogenesis inhibitors, antimetabolites, DNA cleavers, DNA crosslinkers, DNA intercalators, DNA minor groove binders, enediynes, heat shock protein 90 inhibitors, histone deacetylase inhibitors, microtubule stabilizers, nucleoside (purine or pyrimidine) analogs, nuclear export inhibitors, proteasome inhibitors, topoisomerase (I or II) inhibitors, tyrosine kinase inhibitors. Specific anti-cancer or cytotoxic agents include β-lapachone, ansamitocin P3, auristatin, bicalutamide, bleomycin, bortezomib, busulfan, callistatin A, camptothecin, capecitabine, CC-1065, cisplatin, cryptophycins, daunorubicin, disorazole, docetaxel, doxorubicin, duocarmycin, dynemycin A, epothilones, etoposide, floxuridine, floxuridine, fludarabine, fluorouracil, gefitinib, geldanamycin, 17-DMAG, gemcitabine, hydroxyurea, imatinib, interferons, interleukins, irinotecan, maytansine, methotrexate, mitomycin C, oxaliplatin, paclitaxel, suberoylanilide hydroxamic acid (SAHA), thiotepa, topotecan, trichostatin A, vinblastine, vincristine, and vindesine. Preferred combinations are with gefitinib (Iressa®), bortezomib (Velcade®), paclitaxel (Taxol®), docetaxel, thalidomide (Thalomid®), lenalidomide (Revlimid®), and Herceptin®.

Where a course of treatment entails a combination treatment involving 17-AAG and another API, such other API can be administered separately, in its own formulation, or, where amenable, can be administered as an additional component added to a formulation of this invention.

Using a pharmaceutical solution formulation of this invention, 17-AAG can be administered in a dose ranging from about 4 mg/m$^2$ to about 4000 mg/m$^2$, depending on the frequency of administration. A preferred dosage regimen for 17-AAG is about 450 mg/m$^2$ weekly (Banerji et al., *Proc. Am. Soc. Clin. Oncol.* 22, 199 (2003), abstract 797)). Alternatively, a dose of about 308 mg/m$^2$ weekly can be administered. See Goetz et al., *Eur. J. Cancer* 38 (Supp. 7), S54-S55 (2002).

Another dosage regimen is twice weekly, with doses ranging from 220 mg/m$^2$ to 340 mg/m$^2$ (preferably either 220 mg/m$^2$ or 340 mg/m$^2$). A dosage regimen that can be used for combination treatments with another drug, such as docetaxel, is to administer the two drugs every three weeks, with the dose of 17-AAG being up to 650 mg/m$^2$ at each administration.

Formulations of this invention may contain additional excipients. Suitable excipients include carriers, surface active agents, thickening or emulsifying agents, solid binders, dispersion or suspension aids, solubilizers, colorants, flavoring agents, coatings, cryoprotectants, lyoprotectants, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003), the disclosure of which is incorporated herein by reference.

The subject is typically a human, although the methods of the invention can be practiced for veterinary purposes, with suitable adjustment of the unit dose for the particular mammal of interest (including cats, cattle, dogs, horses, and the like).

The practice of this invention can be further understood by reference to the following examples, which are provided by way of illustration and not of limitation.

EXAMPLE 1

Preparation of Purified 17-AAG

This process produces highly pure 17-AAG by removing polar impurities using a slow crystallization from acetone-water at about ambient temperature. A flask containing crude 17-AAG (21 g) was set up for reflux. Acetone (20 mL per gram of solids) was added to the flask. The slurry was brought to reflux and held at that temperature for 5 min. The mixture was cooled to 25° C. over 1 h. Water (in a volume equal to the volume of acetone) was added over a 1 h period. After 20 min, the slurry was filtered. The filter cake was washed with 1:1 acetone:water (40 mL). The wet cake (28 g) was filtered and kept for further processing. The 17-AAG so produced had a chromatographic purity of 99.7% and was Polymorph B.

EXAMPLE 2

Preparation of Purified Polymorph C

This procedure produces 17-AAG predominantly comprising Polymorph C, having high crystallinity. If high purity 17-AAG (such as prepared according to the previous example) is used, the resulting Polymorph C is both highly pure and highly crystalline.

A solution of 17-AAG (1 g, purified according Example 1) in acetone (100 mL) was brought to reflux. Water (100 mL) was added at such a rate as to keep the pot at reflux, or close thereto. Acetone was distilled off until the pot temperature reached 100° C. Additional distillate (20 mL, mostly water) was collected. The pot contents were cooled and the solids collected by filtration using a Buchner funnel fitted with Whatman #52 filter paper and washed with 1:1 acetone:water (20 mL). The crystals were vacuum-dried at >20° C. for >2 h, sampled, and vacuum-dried at 85° C. for about 12 h, yielding Polymorph C.

EXAMPLE 3

Preparation of Purified Polymorph G

A solution of 17-AAG (10.0 g) in acetone (750 mL) was poured into water (1.05 L) at room temperature with stirring. The solution was allowed to stir for an additional 70 min. The Polymorph G crystals were harvested by filtration and dried at 45° C. for 18 h.

In an alternative procedure, 17-AAG (1.0 g) was dissolved in acetone (117 mL) and stirred at room temperature. Water (117 mL) was added at a rate of 15 mL/min. The mixture was stirred for an additional 50 min and the Polymorph G crystals were harvested by filtration and dried at 70° C. for 44 h.

EXAMPLE 4

Analysis and Characterization of 17-AAG Polymorphs

The purity of 17-AAG polymorphs was measured by high-performance liquid chromatography (HPLC), with the following parameters: Zorbax C8 column (4.6×50 mm, 3.5 micron), UV (237 nm) detector, 1.25 mL/min flow rate, 5 μL injection size, acetonitrile as Solvent A, 10 mM ammonium acetate (pH 5.8) as Solvent B, isocratic elution with mobile phase of 45:55 (v:v) Solvent A:Solvent B, 15 min runtime.

XRPD patterns were obtained by Pharmorphix Ltd. (Cambridge, United Kingdom). XRPD patterns of pure 17-AAG Polymorph C and 17-AAG Polymorph C mixed with silicon powder (Aldrich, 60 mesh, Cat. No. 267414-5G) were acquired under identical conditions on a Siemens D5000 diffractometer: CuKα radiation (40 kV, 40 mA), θ-θ goniometer, automatic divergence and receiving slits, a graphite secondary monochromator and a scintillation counter. The data were collected over an angular range of 2° to 42° in 2θ in continuous scan mode using a step size of 0.02° 2θ and a step time of 1 second. Samples were run under ambient conditions and prepared as flat plate specimens using powder as received without grinding. Approximately 25-50 mg of the sample was gently packed into 12 mm diameter, 0.5 mm deep cavities cut into polished, zero-background (510) silicon wafers (The Gem Dugout, 1652 Princeton Drive, Pennsylvania State College, Pa. 16803, USA). All specimens were run both stationary and rotated in their own plane during analysis.

XRPD data are reported using Cu K$\alpha_1$ ($\lambda$=1.5406 Å), after the K$\alpha_2$ component had been stripped using the EVA evaluation program (Brucker Diffrac). The second diffraction pattern was internally referenced to the 111 silicon reflection at 2θ=28.44°. From this the zero point error of the diffractometer was determined to be +0.04°. Exemplary data are presented in FIGS. 1 and 4 and Tables I and II, previously discussed in this specification. Those skilled in the art will appreciate that, depending on parameters such as sample purity and preparation, some scatter in the 2θ angles measured may be expected, on the order of ±0.3 degrees.

Infrared spectra were obtained with a Perkin-Elmer Model 1600 fitted with an ATR accessory. Exemplary infrared spectra are shown in FIGS. 2 and 5, previously discussed in this specification.

DSC data was collected on a TA instruments Q100 or Q1000 machine. The energy and temperature calibration standard was indium. Samples were heated at a rate of 10° C./min between 20 and 250° C. under a nitrogen purge. All samples were scanned in a non-hermetically sealed aluminum pan. Exemplary scans are presented in FIGS. 3 and 6, previously discussed in this specification.

EXAMPLE 5

Formulation with Polysorbate 80

17-AAG (purified Polymorph C, 1.25 g) crystals were mixed with WFI (13 g) and a solution of polysorbate 80 in WFI (3.75 g of a 10 weight % solution in WFI). The mixture was loaded into the reservoir of a Microfluidics Model 110S microfluidizer containing 7 g of WFI and set up with a G10Z interaction chamber equipped with a cooling coil immersed in an ice water bath and processed in recirculation mode for 13 min (640 strokes) at 23 kpsi, with compressed air supplied at a pressure of 100 psi. This procedure yielded a formulation having a 17-AAG concentration of about 50 mg/mL (more exactly, 52.6 mg/mL) in an aqueous medium having approximately 1.5 weight % polysorbate 80, with a 17-AAG particle size distribution (volume distribution) of below 1 micron with median particle size of 300 nm (volume distribution).

Figure 7:
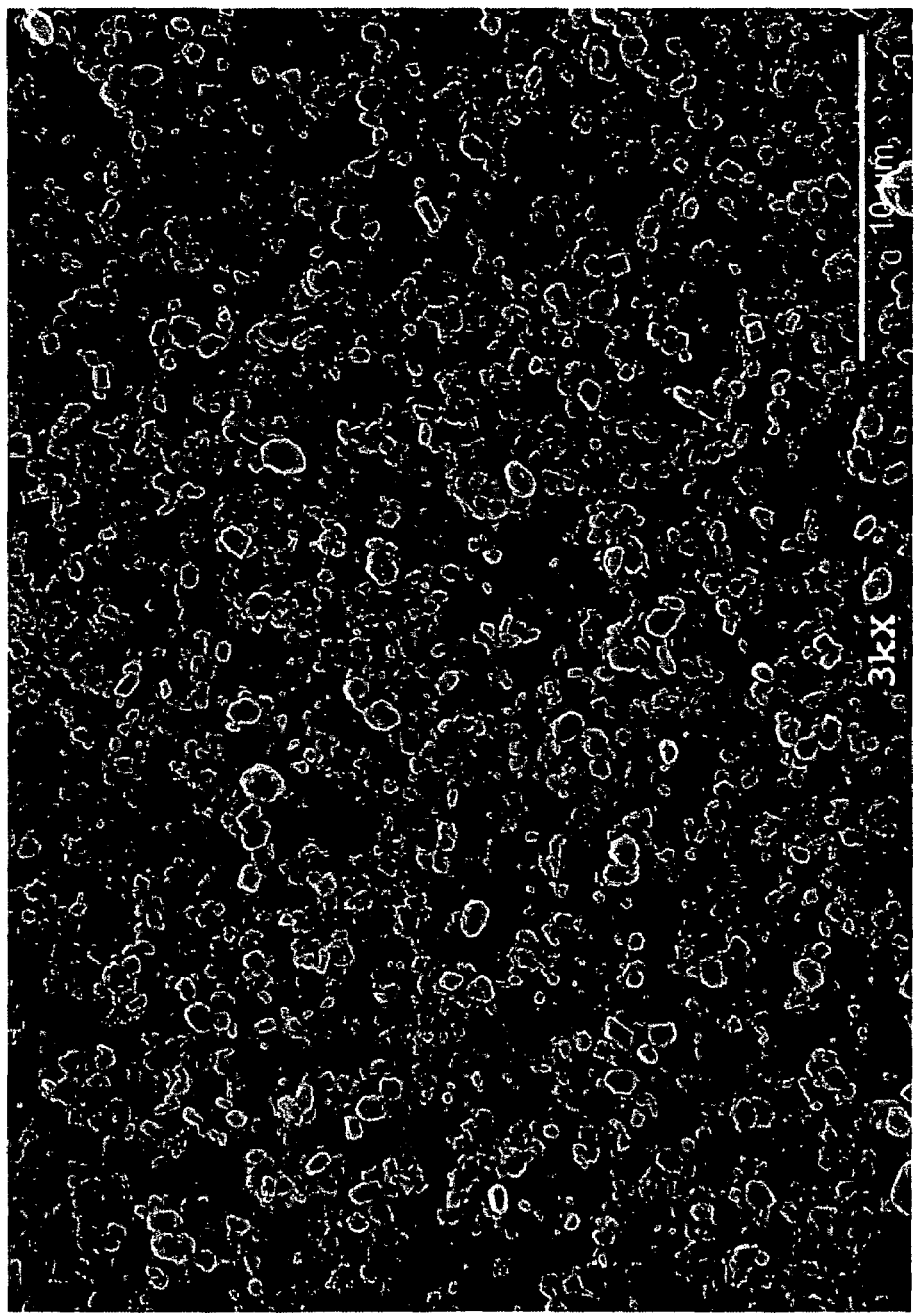
FIG. 7 is a scanning electron microscope (SEM) picture of 17-AAG nanoparticles in a formulation of this invention.

Particle size distribution was determined by dynamic light scattering with a Nanotract 250 particle size analyzer (Microtrac Inc., Montgomeryville, Pa.). The Nanotrac 250 settings were configured for measuring the PSD (volume distribution) of "Irregular" Shaped particles of "Absorbing" Transparency in a fluid with characteristics of water (Refractive Index: 1.333, Viscosity at 20° C.: 0.797 cP, Viscosity at 30° C.: 1.002 cP). A background signal was measured using 5% Dextrose for Injection (D5W). Then, the nanoparticle formulation was diluted 10 to 20-fold into D5W and mixed well. The PSD of the diluted sample was measured as the average of five replicate 5-minute analyses and reported in histogram format as a function of particle size. While the PSD reflects the range and frequency of particle sizes, other characteristics of the PSD were used for quantitation. The D50 is the volume percentile corresponding to the particle size larger than 50% of the total particle volume (i.e. the median particle size). The D90 is the volume percentile corresponding to the particle size larger than 90% of the total particle volume and is a measure of the largest particles in the dispersion. The particle size distribution measured by dynamic light scattering techniques was supplemented with SEM images, acquired by techniques established in the art. The particle sizes determined via the SEM images were in general agreement with those determined by light scattering. FIG. 7 shows a representative SEM image of 17-AAG nanoparticles in one of our formulations.

The processing time was chosen to correspond to approximately 150 passes, using the following relationship:

$$t \cong \frac{150 \times V_{batch}}{r \times V_{stroke}}$$

where
t=total processing time
$V_{batch}$=volume of formulation batch
r=rate (piston strokes/time)
$V_{stroke}$=volume of piston stroke displacement Generally, the number of passes is between about 50 and 200 passes, preferably between about 100 and about 150 passes. A greater number of passes in non-detrimental, but unnecessarily prolongs processing time.

Alternatively, processing time can be determined by assessing particle size distribution at intermediate time points and processing until the desired particle size distribution is attained.

EXAMPLE 6

Formulation with Polysorbate 80 and Phosphatidylcholine

17-AAG (purified Polymorph C, 1.25 g) was mixed with WFI (13.62 g) and a solution of polysorbate 80 solution in WFI (2.5 g of a 10 weight % solution in WFI) and an aqueous suspension of soybean phosphatidylcholine (0.63 g of a 10 weight % suspension in WFI). The mixture was loaded into the reservoir of a Microfluidics Model 110S microfluidizer containing 7 g WFI) and set up as described in the previous example and processed under the same conditions. This procedure yielded a formulation having a 17-AAG concentration of approximately 50 mg/mL in an aqueous medium having approximately 1.0 weight % polysorbate 80 and 0.25 weight % soy phosphatidylcholine, with a 17-AAG particle size distribution of below 1 micron with median particle size of 300 nm (volume distribution).

EXAMPLE 7

Formulation with Polysorbate 80, Phosphatidylcholine and Sucrose

17-AAG (purified Polymorph C, 1.25 g) was mixed with WFI (3.62 g) and a solution of polysorbate 80 (2.5 g of a 10 weight % solution in WFI), an aqueous suspension of soybean phosphatidylcholine (0.63 g of a 10 weight % suspension in WFI), and a solution of sucrose (10 g of a 25 weight % solution in WFI). The mixture was loaded into the reservoir of a Microfluidics Model 110S microfluidizer containing 7 g WFI set up as described in the previous example and processed under the same conditions. This procedure yielded a formulation having a 17-AAG concentration of approximately 50 mg/mL in an aqueous medium having approximately 1.0 weight % polysorbate 80, 0.25 weight % soy phosphatidylcholine, and 10 weight % sucrose, with a 17-AAG particle size distribution of below 1 micron with median particle size of 300 nm volume distribution.

Where a sterile formulation was desired, the polysorbate 80 and sucrose solutions were prepared using WFI and filter sterilized, either as separate solutions or as a solution of the two combined. The phosphatidylcholine suspension was prepared and then autoclaved. The 17-AAG was mixed with a portion of the WFI and autoclaved. The phosphatidylcholine suspension and 17-AAG slurry were autoclaved as separate mixtures or combined as a single mixture. After sterilization, the 17-AAG, the polysorbate® 80 and sucrose solutions, and the phosphatidylcholine mixture were combined aseptically to achieve the desired final composition. The microfluidizer was sterilized (e.g., by autoclaving) and the transfer and processing steps were performed aseptically but otherwise as described in Example 5.

Where it is desired to remove some of the larger particles, centrifugation is the recommended technique. However, centrifugation can cause a corresponding shift in particle size distribution and a loss of up of 40% of the 17-AAG. Filtration can be used to remove outliers—big but infrequent particles—such filtration not affecting perceptibly 17-AAG particle size distribution or assay.

EXAMPLE 8

Effect of Concentration on Homogenizer Throughput

Processing time in a homogenizer is a function of batch volume and the number of passes. Thus, for a given homogenization operation, a given particle should see the same number of passes independent of the particulate concentration, raising the possibility that homogenizer throughput can be increased by using the same number of passes, but with a more concentrated 17-AAG starting suspension.

Figure 8:
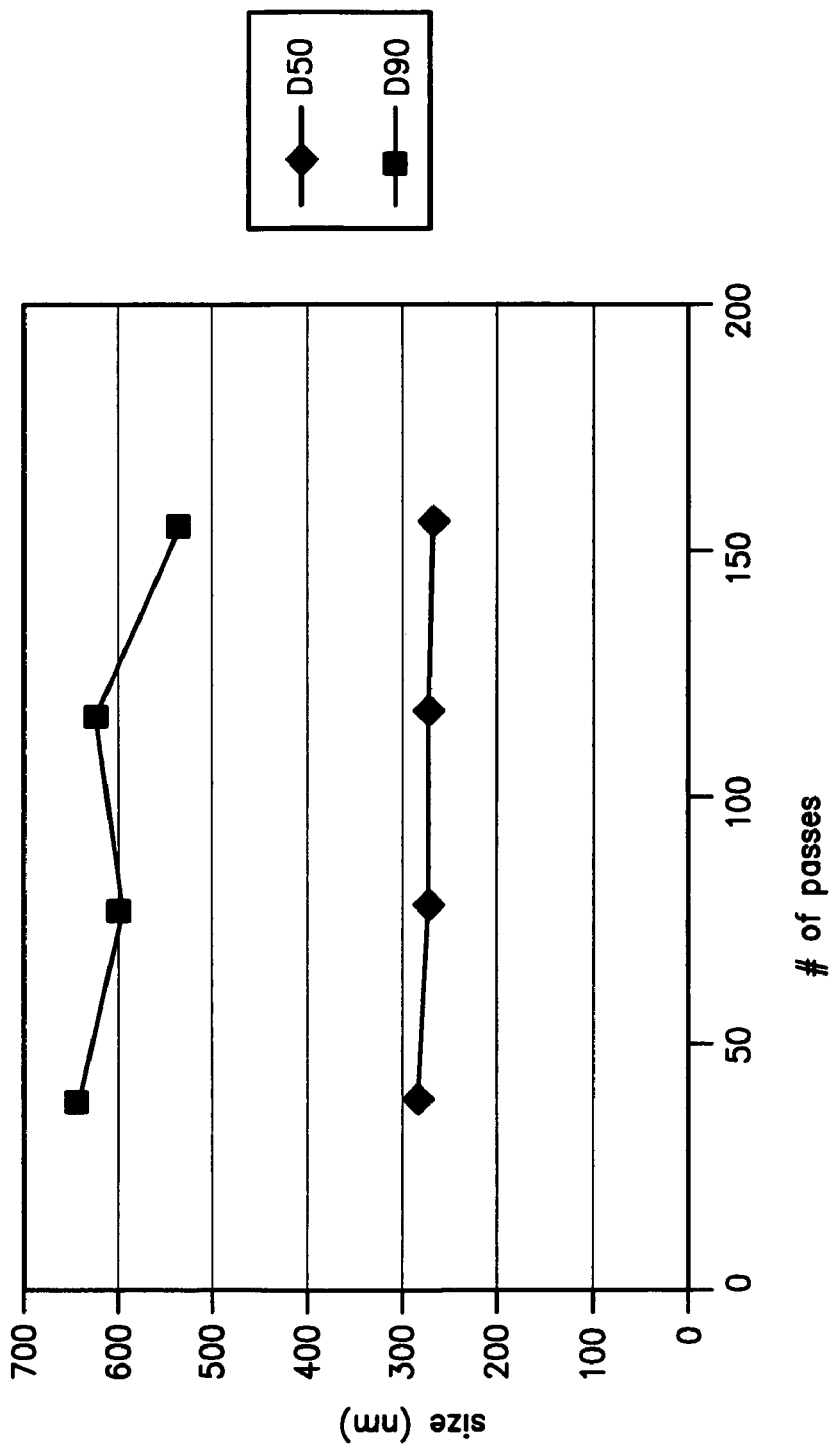
FIG. 8 is plot of particle size as a function of the number of passes for a homogenization batch containing 200 mg/g 17-AAG.

By deferring the addition of the sucrose until post-homogenization dilution and minimizing the amount of water for filter sterilization of polysorbate 80, it was feasible to homogenize formulations containing as much as 200 mg/mL 17-AAG to an acceptable particle size distribution using a similar number of passes as required for a 50 mg/mL concentration. FIG. 8 shows the particle size distribution (both based on D50 and D90) as a function of the number of passes for a batch containing 200 mg/mL 17-AAG. The data show that, after 50 passes, the particle size distribution has leveled out and that, by using batches having a 17-AAG concentration of 200 mg/mL, the homogenizer throughput can be quadrupled.

Thus, the following alternative procedure can be used to produce a formulation of this invention with a higher homogenizer throughput:

(a) A pre-homogenization batch is prepared, containing 200 mg/mL 17-AAG (Polymorph C), 40 mg/mL polysorbate 80, 10 mg/mL Phospholipon® 90G, and balance WFI, for a total batch size of 75 g.
(b) The 17-AAG and Phospholipon 90G are sterilized by autoclaving in water for 60 min.
(c) The polysorbate 80 is filter sterilized as a 25% w/w solution into the sterilized 17-AAG mixture.
(d) The homogenization equipment (Microfluidics MS110) is sterilized by autoclaving for 60 min.
(e) The sterilized materials are added to the sterilized homogenizer and processed (20-23 kpsi pressure, 115-150 passes, interaction chamber G10Z, with cooling coil and bath).
(f) A four-fold dilution of the homogenized suspension into sterile 13% w/w sucrose to produce a final product comprising 50 mg/mL 17-AAG, 10 mg/mL polysorbate 80, 2.5 mg/mL Phospholipon® 90G, and 100 mg/mL sucrose, and balance WFI.

EXAMPLE 9

Formulation with Pluronic®F-68

Nanoparticulate formulations of 17-AAG with Pluronic® F68 polyoxyethylene-polyoxypropylene block copolymer were prepared as described in Example 5 except comprising 5 weight % 17-AAG and between 1.25 and 5 weight % Pluronic® F68 The formulations comprising 2.5 and 5 weight % Pluronic® F68 yielded formulations containing about 50 mg/mL 17-AAG with particle size distributions below 1.2 microns. Both formulations exhibited stable median particle sizes, albeit with possible growth of the largest particles (inconsistent fluctuations in D90 over 24 h).

The 2.5 and 5% formulations were stored at room temperature for eight to nine months and re-evaluated for dispersion stability. Both formulations were re-mixed by vortexing for about 3 min. The sediment in the 2.5% Pluronic® F-68 formulation could not be completely re-suspended, with some material remaining attached to the bottom of the vial. The sediment in the 5% Pluronic® F-68 formulation did re-suspend completely, but some aggregates were visible. Particle size measurements indicated that both formulations consisted of particles predominantly in the 100 to 1,000 nm size range with similar overall size distributions, although they contained large aggregates not measurable with the Nanotrac 250 apparatus. The measured D50s were 360 nm and 390 nm respectively, for the 2.5% Pluronic® F-68 and 5% Pluronic® F-68.

EXAMPLE 10

Formulation with Other Polymorphs

Non-sterile formulations of 17-AAG were made with other polymorphs using the procedure of Example 7 and compared against formulations made with purified Polymorph C. The results provided in Table III show that other forms of 17-AAG lead to inferior formulations, with the exception of purified Polymorph G (albeit resulting in a formulation with a higher D50).

TABLE III

Effect of 17-AAG Starting Polymorph on Formulation Properties

| 17-AAG Polymorph | Consistency | D50 (µm) | Remarks |
|---|---|---|---|
| B (1st run) | Highly viscous | 1.8 | |
| B (2nd run) | Highly viscous | 2.0 | |
| C | Water-like | 0.28 | Stable nanoparticle suspension |
| G | Water-like | 0.36 | D50 higher than for Polymorph C |
| Amorphous (1st run) | Paste-like | n/a | Does not form stable nanoparticle suspension |
| Amorphous (2nd run) | Paste-like | n/a | Does not form stable nanoparticle suspension |

EXAMPLE 11

Lyophilization

For the preparation of formulations that are to be lyophilized, a portion of the WFI was replaced with a corresponding amount of a carbohydrate cryoprotectant solution, as described in the preceding example. For instance, a portion of the WFI can be replaced with an aqueous solution of sucrose to yield final formulations as in the preceding examples, but further containing 10 weight % sucrose. Alternatively, formulations otherwise identical to those described in Examples 4 and 5 but further containing 4 weight % mannitol and 1 weight % sucrose can be prepared by replacing a portion of the WFI with a corresponding amount of a mannitol-sucrose solution.

For lyophilization, the following sequence of steps can be employed:

Freezing:
(a) Cool formulation to +5° C. and hold for 0.5 h
(b) Ramp shelf to −5° C. and hold for another 0.5 h
(c) Ramp shelf to −40° C. at about 1° C./min and hold for 1.5 h Primary Drying
(d) Evacuate to 60 mTorr pressure
(e) Ramp shelf to −25° C. at 1° C./min
(f) Hold at −25° C. for 15 h
(g) Ramp shelf to −28° C. and hold there until primary drying is over based on (i) all product thermocouples reading above −30° C., followed by a delay of 5 h or (ii) an end point of the primary drying is indicated by the differential pressure method (Pirani v. differential capacitance manometer)
(h) Ramp the shelf temperature to 40° C. at a rate of 0.2° C./min
(i) Hold at 40° C. for 6 h

EXAMPLE 12

Storage Stability

Nanoparticulate formulations of this invention were stored over a period of months at either 5° C. or 25° C., to evaluate their stability. The stability of the formulations was evaluated by comparing PSD measured at production to PSD after storage. No significant change in the PSD was observed over a period of several months at either storage condition. Furthermore, no significant change in chemical composition (17-AAG assay and impurity profile) was observed under either storage condition. Ongoing studies show physical and chemical stability over at least nine months.

The stability of the nanoparticle formulation was also tested under conditions of clinical use. In this case, the formulation was diluted 10-fold in D5W, maintained under ambient light and temperature conditions, and sampled over a period of 72 h. No significant change was observed in the diluted formulation in terms of appearance, chemical composition, particle size distribution, osmolality, and pH. These stability studies indicate that the diluted material was completely stable under typical conditions of clinical use.

EXAMPLE 13

Photostability

This example compares the photostability of a dispersion formulation of 17-AAG according to Example 7 compared to a formulation made using Cremophor® (Zhong et al., US 2005/0256097 A1 (2005)).

Each formulation (20 mL) was placed in a vial under separate lamps equipped with a 60 watt soft-white light bulb. The vials were laid horizontally at a distance from the lamps such that the light intensity falling on each was 1,080 light candles, as measured by a calibrated light meter. Each formulation was exposed to light for three days. An aliquot (1 mL) of each formulation was removed each day for analysis, with the 17-AAG content assayed by HPLC. Table IV compares the photostability of the two formulations.

TABLE IV

Photostability of 17-AAG Formulations

| | 17-AAG Assay (%) | |
|---|---|---|
| Day | Dispersion Formulation | Cremophor ™ Formulation |
| 0 | 99.35 | 98.83 |
| 1 | 99.51 | 97.10 |
| 2 | 99.47 | 94.77 |
| 3 | 99.53 | 91.45 |

The above results show that the dispersion formulation according to this invention unexpectedly is much more photostable, retaining essentially a full 17-AAG titer after three days of exposure to light, while the Cremophor®-based formulation has lost about 10% of its 17-AAG titer.

EXAMPLE 14

Pharmacokinetics

This example compares the pharmacokinetic parameters for two formulations, a nanosuspension formulation according to this invention (Formulation A) and a Cremophor®-based formulation (Formulation B). The composition of Formulation A was: 17-AAG (50 mg/mL) aqueous nanosuspension containing additionally polysorbate 80 (1%), lecithin (0.25%), and sucrose (10%). The composition of Formulation B was: 17-AAG in Cremophor® EL (20%), propylene glycol (30%), and ethanol (50%). Each formulation was diluted 10× (Formulation A into D5W; Formulation B into saline) and administered to male beagle dogs by 60 min intravenous infusions or oral gavage, in each instance at a dose of 1.0 mg/kg.

Results are presented in Tables V (infusion) and VI (gavage).

TABLE V

Pharmacokinetic Parameters (Intravenous Infusion)

| Pharmacokinetic Parameter (Geometric Mean) | Formulation A | Formulation B |
| --- | --- | --- |
| $C_{max}$ (ng/mL) | 276.2 | 211.9 |
| $T_{max}$ (hr) | 0.98 | 0.98 |
| $AUC_{inf}$ ((ng–hr)/mL) | 511.8 | 404.5 |
| $T_{1/2}$ (hr) | 2.05 | 2.14 |
| CL (L/hr/kg) | 2.0 | 2.5 |
| $V_z$ (L/kg) | 5.8 | 7.6 |

TABLE VI

Pharmacokinetic Parameters (Oral Gavage)

| Pharmacokinetic Parameter | Formulation A | Formulation B |
| --- | --- | --- |
| $C_{max}$ (ng/mL) | 1.9 | 14.1 |
| $T_{max}$ (hr) | 0.40 | 0.40 |
| $AUC_{inf}$ ((ng–hr)/mL) | 12.3 | 23.8 |
| $T_{1/2}$ (hr) | 5.75 | 2.57 |
| CL/F (L/hr/kg) | 81.5 | 42.0 |
| $V_z/F$ (L/kg) | 676.0 | 155.6 |
| F (%) | 3.0 | 5.9 |

The above results show that both formulations gave very similar plasma exposures via 1-hr intravenous infusion. Greater differences in bioavailability and plasma exposure were noticed when the 17-AAG was administered by oral gavage (for example, bioavailability of 3.0% for Formulation A compared to 5.9% for Formulation A).

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

What is claimed is:

1. Purified Polymorph C of 17-allylamino-17-demethoxygeldanamycin (17-AAG) characterized by:
    (a) an X-ray powder diffraction (XRPD) pattern containing peaks having 2θ values at 6.4±0.3, 8.3±0.3, and 9.6±0.3 degrees; or
    (b) a differential scanning calorimetry (DSC) endothermic transition having an onset temperature in the range between about 188° C. and about 205° C.

2. Purified Polymorph G of 17-allylamino-17-demethoxygeldanamycin (17-AAG) characterized by:
    (a) an X-ray powder diffraction (XRPD) pattern containing peaks having 2θ values at 5.4±0.3, 6.8±0.3, and 7.7±0.3 degrees; or
    (b) a differential scanning calorimetry (DSC) endothermic transition having an onset temperature of about 196° C.

3. A pharmaceutical suspension formulation comprising
    (a) 17-AAG comprising a polymorph selected from: (1) the purified Polymorph C characterized by: (i) an X-ray powder diffraction (XRPD) pattern containing peaks having 2θ values at 6.4±0.3, 8.3±0.3, and 9.6±0.3 degrees, or (ii) a differential scanning calorimetry (DSC) endothermic transition having an onset temperature in the range between about 188° C. and about 205° C.; (2) the purified Polymorph G characterized by: (iii) an X-ray powder diffraction (XRPD) pattern containing peaks having 2θ values at 5.4±0.3, 6.8±0.3, and 7.7±0.3 degrees, or (iv) a differential scanning calorimetry (DSC) endothermic transition having an onset temperature of about 196° C.; and (3) combinations thereof; and
    (b) at least one pharmaceutically acceptable excipient.

4. The pharmaceutical suspension formulation according to claim 3, wherein the polymorph of 17-AAG is the purified Polymorph C characterized by: (a) an X-ray powder diffraction (XRPD) pattern containing peaks having 2θ values at 6.4±0.3, 8.3±0.3, and 9.6±0.3 degrees; or (b) a differential scanning calorimetry (DSC) endothermic transition having an onset temperature in the range between about 188° C. and about 205° C.

5. The pharmaceutical suspension formulation according to claim 3, wherein the polymorph of 17-AAG is the purified Polymorph G characterized by: (a) an X-ray powder diffraction (XRPD) pattern containing peaks having 2θ values at 5.4±0.3, 6.8±0.3, and 7.7±0.3 degrees; or (b) a differential scanning calorimetry (DSC) endothermic transition having an onset temperature of about 196° C.

6. The pharmaceutical suspension formulation according to claim 3, wherein
    (A) the 17-AAG is present in an amount of between about 2.5 to about 75 weight percent as particles suspended in an aqueous medium, the 17-AAG having a particle size distribution between about 50 nm and about 3.0 microns with a median (volume distribution) particle size of between about 200 and about 400 nm, and
    (B) said at least one pharmaceutically acceptable excipient comprises a surface active agent selected from the group consisting of (i) a $C_{12}$-$C_{20}$ fatty acid ester of polyoxyethylene-sorbitan, the weight ratio of the ester to 17-AAG being between about 0.20 and about 1.0, (ii) a polyoxyethylene-polyoxypropylene block copolymer, the weight ratio of the block copolymer to 17-AAG being between about 0.5 and about 1.0, (iii) a phosphatidylcholine, the weight ratio of the phosphatidylcholine to the 17-AAG being between about 0.04 and about 0.1; and (iv) combinations thereof.

7. The pharmaceutical suspension formulation according to claim 6, wherein the polymorph of 17-AAG is the purified Polymorph C characterized by: (a) an X-ray powder diffraction (XRPD) pattern containing peaks having 2θ values at 6.4±0.3, 8.3±0.3, and 9.6±0.3 degrees; or (b) a differential scanning calorimetry (DSC) endothermic transition having an onset temperature in the range between about 188° C. and about 205° C.

8. The pharmaceutical suspension formulation according to claim 6, wherein the polymorph of 17-AAG is the purified Polymorph G characterized by: (a) an X-ray powder diffraction (XRPD) pattern containing peaks having 2θ values at 5.4±0.3, 6.8±0.3, and 7.7±0.3 degrees; or (b) a differential scanning calorimetry (DSC) endothermic transition having an onset temperature of about 196° C.

9. The pharmaceutical suspension formulation according to claim 6, wherein said at least one pharmaceutically acceptable excipient further comprises a carbohydrate.

10. The pharmaceutical suspension formulation according to claim 9, wherein the carbohydrate is sucrose.

11. The pharmaceutical suspension formulation according to claim 6, wherein the surface active agent comprises a combination of a $C_{12}$-$C_{20}$ fatty acid ester of polyoxyethylene-sorbitan and a phosphatidylcholine.

12. The pharmaceutical suspension formulation according to claim 11, wherein the $C_{12}$-$C_{20}$ fatty acid ester of polyoxyethylene-sorbitan is polyoxyethylene-sorbitan monooleate.

13. The pharmaceutical suspension formulation according to claim 6, wherein the surface active agent comprises a combination of a polyoxyethylene-polyoxypropylene block copolymer and a phosphatidylcholine.

14. A method for making a pharmaceutical suspension formulation, comprising homogenizing a mixture of
  (a) 17-AAG comprising a polymorph selected from: (1) the purified Polymorph C characterized by: (i) an X-ray powder diffraction (XRPD) pattern containing peaks having 2θ values at 6.4±0.3, 8.3±0.3, and 9.6±0.3 degrees, or (ii) a differential scanning calorimetry (DSC) endothermic transition having an onset temperature in the range between about 188° C. and about 205° C.; (2) the purified Polymorph G characterized by: (iii) an X-ray powder diffraction (XRPD) pattern containing peaks having 2θ values at 5.4±0.3, 6.8±0.3, and 7.7±0.3 degrees, or (iv) a differential scanning calorimetry (DSC) endothermic transition having an onset temperature of about 196° C.; and (3) combinations thereof, in an amount of between about 2.5 and about 10 weight percent; and
  (b) a surface active agent selected from the group consisting of
    (i) a $C_{12}$-$C_{20}$ fatty acid ester of polyoxyethylene-sorbitan, the weight ratio of the ester to 17-AAG being between about 0.20 and about 1.0,
    (ii) a polyoxyethylene-polyoxypropylene block copolymer, the weight ratio of the block copolymer to 17-AAG being between about 0.5 and about 1.0,
    (iii) a phosphatidylcholine, the weight ratio of the phosphatidylcholine to 17-AAG being between about 0.04 and about 0.1; and
    (iv) combinations thereof,
until the particle size of the 17-AAG is reduced to a particle size distribution between about 50 nm and about 3.0 microns with a median (volume distribution) particle size of between about 200 and about 400 nm.

15. The method according to claim 14, wherein the polymorph of 17-AAG is the purified Polymorph C characterized by:
  (a) an X-ray powder diffraction (XRPD) pattern containing peaks having 2θ values at 6.4±0.3, 8.3±0.3, and 9.6±0.3 degrees; or
  (b) a differential scanning calorimetry (DSC) endothermic transition having an onset temperature in the range between about 188° C. and about 205° C.

16. A method for making a sterile pharmaceutical formulation, comprising the steps of:
  (a) providing a sterile composition comprising 17-AAG selected from: (1) the purified Polymorph C characterized by: (i) an X-ray powder diffraction (XRPD) pattern containing peaks having 2θ values at 6.4±0.3, 8.3±0.3, and 9.6±0.3 degrees, or (ii) a differential scanning calorimetry (DSC) endothermic transition having an onset temperature in the range between about 188° C. and about 205° C.; (2) the purified Polymorph G characterized by: (iii) an X-ray powder diffraction (XRPD) pattern containing peaks having 2θ values at 5.4±0.3, 6.8±0.3, and 7.7±0.3 degrees, or (iv) a differential scanning calorimetry (DSC) endothermic transition having an onset temperature of about 196° C.; and (3) combinations thereof:
  (b) aseptically combining the sterile composition comprising 17-AAG with a sterile solution of a surface active agent selected from the group consisting of (i) a $C_{12}$-$C_{20}$ fatty acid ester of polyoxyethylene-sorbitan, (ii) a polyoxyethylene-polyoxypropylene block copolymer, (iii) a phosphatidylcholine, and (iv) combinations thereof to form sterile mixture; and
  (c) aseptically homogenizing the sterile mixture until the particle size of the 17-AAG is reduced to a particle size distribution between about 50 nm and about 3.0 microns with a median (volume distribution) particle size of between about 200 and about 400 nm.

17. The method according to claim 16, wherein the 17-AAG is the purified Polymorph C characterized by:
  (a) an X-ray powder diffraction (XRPD) pattern containing peaks having 2θ values at 6.4±0.3, 8.3±0.3, and 9.6±0.3 degrees; or
  (b) a differential scanning calorimetry (DSC) endothermic transition having an onset temperature in the range between about 188° C. and about 205° C.

18. A method for preparing purified 17-AAG with higher than 95% purity, comprising the steps of (a) preparing a solution of 17-AAG in refluxing acetone;
  (b) cooling the solution to a temperature in the range between about 18 and about 30 ° C.;
  (c) precipitating the 17-AAG by the addition of an antisolvent portionwise; and (d) collecting the precipitated 17-AAG.

19. A method for making purified Polymorph C of 17-AAG according to claim 1, comprising the steps of
  (a) providing a solution of 17-AAG in acetone, at reflux;
  (b) adding to the solution a volume of water substantially equal to the volume of the solution, at a rate allowing the solution to remain at reflux;
  (c) distilling off the acetone until substantially all the acetone has been distilled off, during which purified Polymorph C precipitates; and
  (d) collecting the purified Polymorph C.

20. Purified Polymorph C of 17-AAG, made by the method of claim 19.

21. The purified Polymorph C of 17-AAG according to claim 1, which is substantially free of other polymorphs of 17-AAG.

22. The purified Polymorph G of 17-AAG according to claim 2, which is substantially free of other polymorphs of 17-AAG.

23. The pharmaceutical suspension formulation according to claim 3, which is stable with respect to particle size distribution (PSD) for at least 9 months.

24. The pharmaceutical suspension formulation according to claim 3, which is stable with respect to appearance, chemical composition, and PSD when diluted 10-fold into 5% dextrose in water and maintained under ambient light and temperature conditions for 72 hr.

25. The pharmaceutical suspension formulation according to claim 3, which maintains at least 99% of its 17-AAG activity after exposure to light at 1080 light candles for three days.

26. A pharmaceutical formulation comprising a polymorph of 17-AAG, said polymorph having at least one of the following analytical characteristics:
   (a) an X-ray powder diffraction (XRPD) pattern in which the lowest angle peaks are at 6.4±0.3, 8.3±0.3 and 9.6±0.3 degrees 2θ; or
   (b) a differential scanning calorimetry (DSC) endothermic transition having an onset temperature in the range between about 188° C. and about 205° C., without the occurrence of any other DSC thermal events at a lower temperature.

27. The pharmaceutical formulation according to claim 26, wherein said polymorph has the infrared spectrum of FIG. 2.

28. The pharmaceutical formulation according to claim 26, that is a lyophilate.

29. The pharmaceutical formulation according to claim 26, that is a suspension suitable for intravenous administration.

30. A pharmaceutical formulation comprising a polymorph of 17-AAG, said polymorph having at least one of the following analytical characteristics:
   (a) an X-ray powder diffraction (XRPD) pattern with peaks at 5.4±0.3, 6.8±0.3, 7.7±0.3, 8.9±0.3, 9.6±0.3, and 10.7±0.3 degrees 2θ; or
   (b) a differential scanning calorimetry (DSC) endothermic transition having an onset temperature of about 196° C.

31. The pharmaceutical formulation according to claim 30, wherein said polymorph has the infrared spectrum of FIG. 5.

32. The pharmaceutical formulation according to claim 30, that is a lyophilate.

33. The pharmaceutical formulation according to claim 30, that is a suspension suitable for intravenous administration.

34. A pharmaceutical suspension formulation comprising 17-AAG selected from: (1) the purified Polymorph C characterized by: (i) an X-ray powder diffraction (XRPD) pattern containing peaks having 2θ values at 6.4±0.3, 8.3±0.3, and 9.6±0.3 degrees, or (ii) a differential scanning calorimetry (DSC) endothermic transition having an onset temperature in the range between about 188° C. and about 205° C.; (2) the purified Polymorph G characterized by: (iii) an X-ray powder diffraction (XRPD) pattern containing peaks having 2θ values at 5.4±0.3, 6.8±0.3, and 7.7±0.3 degrees, or (iv) a differential scanning calorimetry (DSC) endothermic transition having an onset temperature of about 196° C.; and (3) combinations thereof and at least one pharmaceutically acceptable excipient, wherein
   (A) the 17-AAG is present in an amount of between about 2.5 to about 75 weight percent as particles suspended in an aqueous medium, the 17-AAG having a particle size distribution between about 50 nm and about 3.0 microns with a median (volume distribution) particle size of between about 200 and about 400 nm, and
   (B) said at least one pharmaceutically acceptable excipient comprises a surface active agent selected from the group consisting of (i) a $C_{12}C_{20}$ fatty acid ester of polyoxyethylene-sorbitan, the weight ratio of the ester to 17-AAG being between about 0.20 and about 1.0, (ii) a polyoxyethylene-polyoxypropylene block copolymer, the weight ratio of the block copolymer to 17-AAG being between about 0.5 and about 1.0, (iii) a phosphatidyicholine, the weight ratio of the phosphatidyicholine to the 17-AAG being between about 0.04 and about 0.1; and (iv) combinations thereof;
said pharmaceutical suspension formulation being stable with respect to particle size distribution (PSD) for at least 9 months.

35. The pharmaceutical suspension formulation according to claim 34, wherein the 17-AAG is the purified Polymorph C of 17-AAG characterized by: (a) an X-ray powder diffraction (XRPD) pattern containing peaks having 2θ values at 6.4±0.3. 8.3±0.3, and 9.6±0.3 degrees; or (b) a differential scanning calorimetry (DSC) endothermic transition having an onset temperature in the range between about 188° C. and about 205° C.

36. The pharmaceutical suspension formulation according to claim 34, wherein the 17-AAG is the purified Polymorph G of 17-AAG characterized by: (a) an X-ray powder diffraction (XRPD) pattern containing peaks having 2θ values at 5.4±0.3, 6.8±0.3, and 7.7±0.3 degrees; or (b) a differential scanning calorimetry (DSC) endothermic transition having an onset temperature of about 196° C.

37. A pharmaceutical suspension formulation comprising 17-AAG selected from: (1) the purified Polymorph C characterized by: (i) an X-ray powder diffraction (XRPD) pattern containing peaks having 2θ values at 6.4±0.3, 8.3±0.3, and 9.6±0.3 degrees, or (ii) a differential scanning calorimetry (DSC) endothermic transition having an onset temperature in the range between about 188° C. and about 205° C.; (2) the purified Polymorph G characterized by: (iii) an X-ray powder diffraction (XRPD) pattern containing peaks having 2θ values at 5.4±0.3, 6.8±0.3, and 7.7±0.3 degrees, or (iv) a differential scanning calorimetry (DSC) endothermic transition having an onset temperature of about 196° and (3) combinations thereof and at least one pharmaceutically acceptable excipient, wherein
   (A) the 17-AAG is present in an amount of between about 2.5 to about 75 weight percent as particles suspended in an aqueous medium. the 17-AAG having a particle size distribution (PSD) between about 50 nm and about 3.0 microns with a median (volume distribution) particle size of between about 200 and about 400 nm, and
   (B) said at least one pharmaceutically acceptable excipient comprises a surface active agent selected from the group consisting of (i) a $C_{12}$-$C_{20}$ fatty acid ester of polyoxyethylene-sorbitan, the weight ratio of the ester to 17-AAG being between about 0.20 and about 1.0, (ii) a polyoxyethylene-polyoxypropylene block copolymer, the weight ratio of the block copolymer to 17-AAG being between about 0.5 and about 1.0, (iii) a phosphatidylcholine, the weight ratio of the phosphatidyicholine to the 17-AAG being between about 0.04 and about 0.1; and (iv) combinations thereof;
said pharmaceutical suspension formulation being stable with respect to appearance, chemical composition, and PSD when diluted 10-fold into 5% dextrose in water and maintained under ambient light and temperature conditions for 72 hr.

38. The pharmaceutical suspension formulation according to claim 37, wherein the 17-AAG is the purified Polymorph C of 17-AAG characterized by: (a) an X-ray powder diffraction (XRPD) pattern containing peaks having 2θ values at 6.4±0.3, 8.3±0.3, and 9.6±0.3 degrees; or (b) a differential scanning calorimetry (DSC) endothermic transition having an onset temperature in the range between about 188° C. and about 205° C.

39. The pharmaceutical suspension formulation according to claim 37, wherein the 17-AAG is the purified Polymorph G of 17-AAG characterized by: (a) an X-ray powder diffraction (XRPD) pattern containing peaks having 2θ values at 5.4±0.3, 6.8±0.3, and 7.7±0.3 degrees; or (b) a differential scanning calorimetry (DSC) endothermic transition having an onset temperature of about 196° C.

40. A pharmaceutical suspension formulation comprising 17-AAG selected from: (1) the purified Polymorph C characterized by: (i) an X-ray powder diffraction (XRPD) pattern containing peaks having 2θ values at 6.4±0.3, 8.3±0.3, and 9.6±0.3 degrees, or (ii) a differential scanning calorimetry (DSC) endothermic transition having an onset temperature in the range between about 188° C. and about 205° C.; (2) the purified Polymorph G characterized by: (iii) an X-ray powder diffraction (XRPD) pattern containing peaks having 2θ values at 5.4±0.3, 6.8±0.3, and 7.7±0.3 degrees, or (iv) a differential scanning calorimetry (DSC) endothermic transition having an onset temperature of about 196° C.; and (3) combinations thereof and at least one pharmaceutically acceptable excipient, wherein
  (A) the 17-AAG is present in an amount of between about 2.5 to about 75 weight percent as particles suspended in an aqueous medium, the 17-AAG having a particle size distribution (PSD) between about 50 nm and about 3.0 microns with a median (volume distribution) particle size of between about 200 and about 400 nm, and
  (B) said at least one pharmaceutically acceptable excipient comprises a surface active agent selected from the group consisting of (i) a $C_{12}$-$C_{20}$ fatty acid ester of polyoxyetbylene-sorbitan, the weight ratio of the ester to 17-AAG being between about 0.20 and about 1.0, (ii) a polyoxyethylene-polyoxypropylene block copolymer, the weight ratio of the block copolymer to 17-AAG being between about 0.5 and about 1.0, (iii) a phosphatidylcholine, the weight ratio of the phosphatidyicholine to the 17-AAG being between about 0.04 and about 0.1; and (iv) combinations thereof,
said pharmaceutical suspension formulation maintaining at least 99% of its 17-AAG activity after exposure to light at 1080 light candles for three days.

41. The pharmaceutical suspension formulation according to claim 40, wherein the 17-AAG is the purified Polymorph C of 17-AAG characterized by: (a) an X-ray powder diffraction (XRPD) pattern containing peaks having 2θ values at 6.4±0.3, 8.3±0.3, and 9.6±0.3 degrees; or (b) a differential scanning calorimetry (DSC) endothermic transition having an onset temperature in the range between about 188° C. and about 205° C.

42. The pharmaceutical suspension formulation according to claim 40, wherein the 17-AAG is the purified Polymorph G of 17-AAG characterized by: (a) an X-ray powder diffraction (XRPD) pattern containing peaks having 2θ values at 5.4±0.3, 6.8±0.3, and 7.7±0.3 degrees: or (b) a differential scanning calorimetry (DSC) endothermic transition having an onset temperature of about 196° C.

43. A pharmaceutical suspension formulation comprising 17-AAG selected from: (1) the purified Polymorph C characterized by: (i) an X-ray powder diffraction (XRPD) pattern containing peaks having 2θ values at 6.4±0.3, 8.3±0.3, and 9.6±0.3 degrees, or (ii) a differential scanning calorimetry (DSC) endothermic transition having an onset temperature in the range between about 188° C. and about 205° C.; (2) the purified Polymorph G characterized by: (iii) an X-ray powder diffraction (XRPD) pattern containing peaks having 2θ values at 5.4±0.3, 6.8±0.3, and 7.7±0.3 degrees, or (iv) a differential scanning calorimetry (DSC) endothermic transition having an onset temperature of about 196° C.; and (3) combinations thereof and at least one pharmaceutically acceptable excipient, wherein
  (A) the 17-AAG is present in an amount of between about 2.5 to about 10 weight percent as particles suspended in an aqueous medium, the 17-AAG having a particle size distribution (PSD) between about 50 nm and about 3.0 microns with a median (volume distribution) particle size of between about 200 and about 400 nm, and
  (B) said at least one pharmaceutically acceptable excipient comprises a surface active agent selected from the group consisting of (i) polyoxyethylene-sorbitan monooleate, whose weight ratio to 17-AAG is between about 0.20 and about 0.35, (ii) a polyoxyethylene-polyoxypropylene block copolymer, the weight ratio of the block copolymer to 17-AAG being between about 0.5 and about 1.0, (iii) a phosphatidylcholine, the weight ratio of the phosphatidyicholine to the 17-AAG being between about 0.04 and about 0.06; and (iv) combinations thereof.

44. A method of making Polymorph G of 17-AAG according to claim 2, comprising the steps of
  (a) providing a solution of 17-AAG in acetone;
  (b) combining the solution with water to separate out Polymorph G; and
  (c) harvesting the Polymorph G.

45. Polymorph G of 17-AAG, made by the method of claim 44.

46. Polymorph B of 17-AAG, having XRPD peaks at about 5.9, 6.3, 7.2, 7.5. 9.3, 9.8, 11.6, and 12.5 degrees 2θ.

47. A method of making Polymorph C of 17-AAG, comprising the step of heating the Polymorph B of 17-AAG of claim 46.

* * * * *